(12) United States Patent
Andrews et al.

(10) Patent No.: US 12,189,106 B2
(45) Date of Patent: Jan. 7, 2025

(54) MICROINSTRUMENT SYSTEM AND METHOD FOR RECORDING AN IMAGE BY FIBRE-OPTIC SCANNING, AND COMPUTER-IMPLEMENTED METHOD FOR GENERATING AN IMAGE

(71) Applicant: CARL ZEISS MEDITEC AG, Jena (DE)

(72) Inventors: Delbert Peter Andrews, Oberkochen (DE); Christian Voigt, Oberkochen (DE); Carolin Klusmann, Oberkochen (DE); Matthias Hillenbrand, Oberkochen (DE); Max Riedel, Oberkochen (DE); Christian Marzi, Oberkochen (DE); Franziska Mathis-Ullrich, Oberkochen (DE); Fritz Hengerer, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/556,195

(22) PCT Filed: Apr. 14, 2022

(86) PCT No.: PCT/EP2022/060131
§ 371 (c)(1),
(2) Date: Oct. 19, 2023

(87) PCT Pub. No.: WO2022/223469
PCT Pub. Date: Oct. 27, 2022

(65) Prior Publication Data
US 2024/0329376 A1    Oct. 3, 2024

(30) Foreign Application Priority Data
Apr. 19, 2021  (DE) .................... 10 2021 109 825.4

(51) Int. Cl.
*G02B 26/10* (2006.01)
*A61B 3/10* (2006.01)
(Continued)

(52) U.S. Cl.
CPC .......... *G02B 21/0032* (2013.01); *A61B 3/102* (2013.01); *A61B 5/0066* (2013.01);
(Continued)

(58) Field of Classification Search
CPC ............ G02B 21/0032; G02B 21/0012; G02B 21/0036; G02B 21/0056; G02B 21/008;
(Continued)

(56) References Cited

U.S. PATENT DOCUMENTS

| 6,294,775 B1 | 9/2001 | Seibel et al. |
| 7,189,961 B2 | 3/2007 | Johnston et al. |

(Continued)

FOREIGN PATENT DOCUMENTS

| CN | 108873135 A | 11/2018 |
| EP | 3288465 B1 | 2/2019 |

(Continued)

OTHER PUBLICATIONS

JP Office Action for App. No. 2023-564031, dated May 21, 2024 (7 pages).

(Continued)

*Primary Examiner* — Nguyen T Truong
(74) *Attorney, Agent, or Firm* — NIXON PEABODY LLP; Jeffrey L. Costellia

(57) ABSTRACT

A microinstrument system comprises: a microinstrument, having at least one integrated optical fiber which has a distal end facing the object to be observed; a recording apparatus, to which light from the object to be observed can be supplied for recording image data with the aid of the at least one optical fiber; a determining device, which is designed to (Continued)

determine the positions of the distal end of the at least one optical fiber at the recording times of the particular image data; wherein a data-processing device, connected to the recording apparatus in order to receive the image data; is connected to the determining device in order to receive the position data; and is designed to compile the image data with the aid of the position data to form a two-dimensional or three-dimensional image.

32 Claims, 9 Drawing Sheets

(51) Int. Cl.
  *A61B 5/00* (2006.01)
  *G02B 21/00* (2006.01)
  *G02B 21/36* (2006.01)
(52) U.S. Cl.
  CPC ........ *A61B 5/0084* (2013.01); *G02B 21/0012* (2013.01); *G02B 21/0036* (2013.01); *G02B 21/0056* (2013.01); *G02B 21/008* (2013.01); *G02B 21/361* (2013.01); *G02B 26/103* (2013.01)
(58) Field of Classification Search
  CPC .... G02B 21/361; G02B 26/103; A61B 3/102; A61B 5/0066; A61B 5/0084
  USPC .......................................................... 348/46
  See application file for complete search history.

(56) References Cited

U.S. PATENT DOCUMENTS

| | | |
|---|---|---|
| 10,045,882 B2 | 8/2018 | Balicki et al. |
| 10,517,760 B2 | 12/2019 | Berlin |
| 2005/0027199 A1 | 2/2005 | Clarke |
| 2007/0239033 A1 | 10/2007 | Tearney et al. |
| 2008/0161648 A1 | 7/2008 | Karasawa |
| 2013/0077048 A1 | 3/2013 | Mirlay |
| 2013/0123759 A1 | 5/2013 | Kang et al. |
| 2015/0173606 A1 | 6/2015 | Yu et al. |
| 2015/0297404 A1 | 10/2015 | Kang et al. |
| 2018/0103842 A1 | 4/2018 | Parto et al. |
| 2018/0360310 A1 | 12/2018 | Berlin |
| 2020/0107886 A1 | 4/2020 | Govari et al. |
| 2021/0059519 A1 | 3/2021 | Hara et al. |

FOREIGN PATENT DOCUMENTS

| | | |
|---|---|---|
| GB | 2551102 A | 12/2017 |
| JP | 2008165236 A | 7/2008 |
| JP | 2017501854 A | 1/2017 |
| JP | 2019532730 A | 11/2019 |
| JP | 2020524061 A | 8/2020 |
| WO | 02083003 A1 | 10/2002 |
| WO | 2012012540 A2 | 1/2012 |
| WO | 2012126070 A1 | 9/2012 |
| WO | 2014175853 A1 | 10/2014 |
| WO | 2016001689 A1 | 1/2016 |
| WO | 2016016891 A1 | 2/2016 |
| WO | 2020140042 A1 | 7/2020 |
| WO | 2020167678 A1 | 8/2020 |

OTHER PUBLICATIONS

Hendriks et al., "High-resolution resonant and nonresonant fiber-scanning confocal microscope," Journal of Biomedical Optics, vol. 16, No. 2, Feb. 2011, pp. 026007-1-026007-8.
Kang et al., "Demonstration of Subretinal Injection Using Common-Path Swept Source OCT Guided Microinjector," Applied Sciences, 2018, No. 8, pp. 1-11.
German Office Action for Application No. 10 2021 109 825.4, mailed Jan. 25, 2022 (17 pages).
International Preliminary Report for Application No. PCT/EP2022/060131, mailed Aug. 7, 2023 (34 pages).
International Search Report for Application No. PCT/EP2022/060131, mailed Aug. 23, 2022 (5 pages).
Written Opinion for Application No. PCT/EP2022/060131, mailed Aug. 23, 2022, with machine translation (16 pages).

MICROINSTRUMENT SYSTEM AND METHOD FOR RECORDING AN IMAGE BY FIBRE-OPTIC SCANNING, AND COMPUTER-IMPLEMENTED METHOD FOR GENERATING AN IMAGE

CROSS-REFERENCE TO RELATED APPLICATIONS

The present application is the U.S. National Stage entry of International Application No. PCT/EP2022/060131, filed Apr. 14, 2022, which claims priority under 35 U.S.C. § 119 to German Patent Application No. 10 2021 109 825.4, filed Apr. 19, 2021, the contents of which are incorporated by reference herein in their entirety.

The present invention relates to a microinstrument system and its use for recording a two-dimensional or three-dimensional image by fiber-optic scanning. Additionally, the invention relates to a computer-implemented method for generating a two-dimensional or three-dimensional image of an observation object.

There is an intraoperative visualization of the operating site using a surgical microscope in some fields of surgery, for example in neurosurgery and ophthalmic surgery. Moreover, the surgical microscope can also be equipped with an apparatus for performing optical coherence tomography (OCT), with the aid of which a region of interest of the operating site is scanned using a finely focused beam. However, such purely external imaging has certain limitations if hard-to-access structures, for example in the eye, are intended to be visualized. Thus, for instance, the trabecular meshwork or regions behind the iris such as the peripheral retina, the ora serrata, the pars plana, the ciliary body region or the sulcus in the eye cannot be visualized and/or measured directly or can only be directly visualized and/or measured with difficulties on account of shadowing effects or geometric limitations. Moreover, there are situations where the visualization of the operating site using external imaging would be possible in principle but is prevented on account of certain circumstances. Thus, external visualization is greatly impaired or not at all possible in the case of, for instance, an ophthalmic surgical procedure in the posterior eye region with a cloudy vitreous humor, a corneal opacification or a vitreous humor hemorrhage. Such limitations in the intraoperative visualization based on a surgical microscope present great challenges to the surgeon and may also have a negative effect on the possibilities or the results of a surgical procedure. For some cases, ophthalmic surgery knows of a simple method for overcoming the aforementioned problem, specifically what is known as scleral indentation and depression of the eye in order to make otherwise shadowed structures accessible to imaging. However, this method harbors a risk of tissue trauma. Moreover, imaging stability is not always simple due to a lack of sufficient control of the indentation. A further significant disadvantage of this method is that a free hand must be available to indent the eye. Moreover, the indentation is not always suitable for supplying the obstructed locations in the eye to a visualization. Neurosurgical methods may also be hampered by obstructed locations not readily being able to be supplied to imaging by way of the displacement of tissue.

Fiber-optic OCT systems constitute an option for supplying obstructed structures in the operating site to imaging. Such a fiber-optic OCT system is described in U.S. Pat. No. 10,517,760 B2, for example. The OCT system described in U.S. Pat. No. 10,517,760 B2 is used in OCT-guided glaucoma operations, wherein intraocular imaging can be implemented using a fiber-optic OCT system. In this case, an optical fiber or an optical fiber bundle is integrated in a fiber-optic probe which can be inserted into the interior of the eye. One-dimensional scans and, should a fiber bundle be used, two-dimensional and three-dimensional scans are possible using such a fiber-optic OCT system.

GB 2551102 A describes a surgical instrument in which one or more optical fibers of an OCT system are integrated. Two-dimensional or three-dimensional images can be recorded with the aid of the optical fibers.

WO 2012/0126070 A1 and WO 2014/0175853 A1 describe what are known as pullback methods, in which an OCT probe is inserted into a blood vessel and then pulled back. Three-dimensional images of the blood vessel are acquired by means of the OCT probe during the pullback.

WO 2016/01689 A1 has moreover disclosed the production of a 3-D image or a map by means of an OCT system comprising a fiber with a scanning head; and US 2007/0239033 A1 and WO 02/083003 A1 have disclosed biopsy needles with integrated optical fibers.

Moreover, US 2013/0077048 A1 describes imaging by means of a fiber camera, with the diameter of the fibers used being between 0.5 and 2 mm.

Moreover, the practice of determining the distance of the tip of a microsurgical instrument from a target location of the instrument with the aid of fiber-optic OCT systems is known. Such methods and apparatuses are described in WO 2012/012540 A2, US 2015/0297404 A1, and U.S. Pat. No. 10,045,882 B2, for example.

The described methods require either a fiber bundle for producing a two-dimensional or three-dimensional image or a scanning device at the distal fiber end, by means of which a lateral scan can be performed. When a fiber bundle is used, the lateral extent thereof is restricted by the free lumen of the microinstrument, with the result that the two-dimensional or three-dimensional image can only depict a relatively small lateral region of the operating site with the best possible resolution, especially whenever very small microinstruments are used. Although the depicted lateral region could be increased using a suitable attachment optical unit, this would worsen the resolution. The use of a scanner in the region of the distal fiber end moreover leads to a mechanically complex distal structure of the microinstrument, which may render a disinfection of the microinstrument difficult or even impossible and greatly restricts the minimal size thereof. Moreover, production costs also increase with the complexity of the structure, whereby the economic attractiveness of such a solution is reduced. Moreover, the distal components must be ever larger and more complex, the greater the detection or scanning region should be. If by contrast the distal end is intended to be kept small, only a very restricted performance of the imaging is possible, for example in view of a large extent of the possible scanning regions in combination with a high resolution.

Recording three-dimensional images within the scope of the pullback method is predominantly suitable for recording images of tubular objects, and not so suitable for recording images of planar objects.

Hence there is a need for a microinstrument system and a method for recording two-dimensional or three-dimensional images by fiber-optic scanning, the system and method allowing two-dimensional or three-dimensional images to be recorded using a single optical fiber or allowing two-dimensional or three-dimensional images to be recorded using a fiber bundle, these images showing an object region which has a greater lateral extent than the fiber bundle, and moreover having little complexity at the distal end of the microinstrument.

This object is achieved by a microinstrument system as claimed in claim 1, a computer-implemented method for generating a two-dimensional or three-dimensional image as claimed in claim 9, and a method for recording a two-dimensional or three-dimensional image by fiber-optic scanning as claimed in claim 14. The dependent claims contain advantageous configurations of the invention.

A microinstrument system according to the invention for recording a two-dimensional or three-dimensional image of an observation object by fiber-optic scanning while the distal end of at least one optical fiber is moved laterally over the region of interest of the observation object with the aid of a microinstrument comprises:

A microinstrument having at least one integrated optical fiber, which has a distal end to face the observation object. In this case, the at least one optical fiber can be an optical fiber of a fiber-optic OCT system in particular. However, it may alternatively also be part of a fiber-optic confocal microscope.

A recording apparatus to which, for the purpose of recording image data from the observation object is suppliable with the aid of the at least one optical fiber. In this case, the image data can be individual pixels, which is to say individual picture elements in a two-dimensional image, or voxels, which is to say individual picture elements in a three-dimensional image, when using a single optical fiber for scanning the observation object, or else be individual A-scans, which is to say a plurality of picture elements originating from different depths of the observation object, if the optical fiber is part of a fiber-optic OCT system. The image data can be small-area 2-D images if a fiber bundle is used to scan the observation object or small-volume 3-D images if the fiber bundle is part of a fiber-optic OCT apparatus. The lateral extent of the area represented by the individual image data or of the volume represented by the individual image data in this case corresponds to the extent of the distal end of the fiber bundle.

A determination device designed to determine at least position data which represent the position of the distal end of the at least one optical fiber at the recording times of the respective image data and to assign said position data to the image data. In this case, the determination device can be designed to detect the position of the distal end of the at least one optical fiber at the recording times of the respective image data during a scan. In this case, use can be made of for example an optical tracking system or an inertial sensor system as the determination device, which determines the position on the basis of detected movements or on the basis of the detected orientations should only a rotation about a point of rotation be possible. As an alternative or in addition, the determination device can be designed to determine the position data of the distal end of the at least one optical fiber at the recording times of the respective image data by calculation during a scan, using as a basis collected data from which the positions of the distal end of the at least one optical fiber at the recording times of the respective image data can be derived. For example, if different positions of the distal end of the microinstrument are based on a rotation of the microinstrument about a point of rotation, then the position of the distal end of the microinstrument can be determined on the basis of the orientation of the microinstrument and the distance between the point of rotation and its distal end. Accordingly, the data from which the position data of the distal end of the at least one optical fiber can be derived when the respective image data are acquired can be orientation data. In principle, determining the position data of the distal end of the at least one optical fiber on the basis of stereoscopic images showing the distal end in relation to the observation object is also possible. The data from which the position data of the distal end of the at least one optical fiber can be derived when the respective image data are acquired are the data from the stereoscopic images in that case.

According to the invention, the data processing device is connected to the recording apparatus for the purpose of receiving the image data and connected to the determination device for the purpose of receiving the position data. It is designed to compile the image data to form a two-dimensional or three-dimensional image with the aid of the position data.

It is also advantageous if the determination device is designed to also determine orientation data which represent the orientation of the distal end of the at least one optical fiber at the recording times of the respective image data and to assign said orientation data to the image data, and the data processing device is also connected to the determination device for the purpose of receiving the orientation data. Then, the data processing device is designed to compile the image data to form a two-dimensional or three-dimensional image not only with the aid of the position data but also with the aid of the orientation data. It may be sensible to determine the orientation data especially whenever the orientation of the distal end of the at least one optical fiber changes beyond a given limit of allowed orientation fluctuations with its position during a scan. In this case, the given limit of allowed orientation fluctuations may depend on the resolution with which the image data are collected and optionally on the depth range over which an A-scan is implemented. It should be chosen in such a way that, for the entire depth range of an A-scan, the allowed orientation fluctuations of the distal end of the at least one optical fiber lead only to fluctuations in the locations at which the image data for the A-scan are acquired, which are smaller than the spatial resolution of the acquired image data.

A synchronization device may be present to assign the position data and optionally the orientation data to the image data; it is designed to synchronize, firstly, the position data and optionally the orientation data and, secondly, the image data with one another in time.

The microinstrument system according to the invention allows a two-dimensional or three-dimensional image of an observation object to be recorded by way of a scan with a small number of optical fibers and even with only a single optical fiber, the image reflecting a lateral region of the observation object which is significantly larger than the extent of the distal end of the at least one optical fiber or of the distal end of the fiber bundle used. To this end, for scanning purposes, the user need only move the distal end of the microinstrument over the region of interest of the observation object in a sweeping movement, as if they wanted to paint the observation object. Image data are acquired at a multiplicity of positions of the distal end of the at least one optical fiber during this sweeping movement and are then used to construct a two-dimensional or three-dimensional image point-by-point with the aid of the position data assigned to the image data and, if necessary, with the aid of the orientation data. The scan can be used to compile a large two-dimensional or three-dimensional image from individual two-dimensional or three-dimensional images respectively reproducing a small lateral region of the observation object if it is not a single optical fiber but a fiber bundle that is used. Moreover, if a fiber bundle is used, it is also possible in part to successively detect object regions by means of a plurality of fibers of the fiber bundle during the sweeping movement, with the result that the signal intensity can be increased and hence the signal-to-noise ratio can be improved. Since the relative positions of the distal ends of the individual optical fibers of the fiber bundle are known relative to one another, it is sufficient to detect or determine the position and optionally the orientation of the distal end of one individual optical fiber of the fiber bundle. The positions and orientation of the remaining fibers can then be determined from the known spatial relationship between the distal ends of the individual optical fibers in the fiber bundle.

The microinstrument system according to the invention requires no scanner at the distal end of the at least one optical fiber, with the result that the structure of the microinstrument can be kept simple, facilitating the sterilization of said microinstrument. Additionally, the simple structure enables a cost-effective production of the microinstrument as a disposable product, and this can ensure the sterility of the instrument better than in the case of the re-sterilization of used instruments, especially in the case of very small structural dimensions. However, a scanner at the distal end of the at least one optical fiber is possible as an option.

The position and/or the orientation of the distal end of the at least one optical fiber can either be detected directly, for example by means of a tracking system or an inertial sensor system, or by virtue of the distal end of the at least one optical fiber being recognized in stereoscopic images, or be detected indirectly, by virtue of the position and/or the orientation of an element of the microinstrument, for instance a marker arranged on the microinstrument, being detected, with the spatial position and optionally the orientation of said marker being known in relation to the distal end of the at least one optical fiber. Moreover, there is the option of determining the position data and/or the orientation data in absolute terms, which is to say in a defined coordinate system, or of determining these relatively, for example relative to the object (for instance, by detecting distances and orientations with respect to the object) or relative to one another (for instance on the basis of the same image content in successive image data). Moreover, the position data and/or the orientation data can be used to set position-dependent parameters of the image recording, for instance the focus, or to position and/or orient the at least one fiber for the scan.

In this case, it is not mandatory for a position measurement to also be implemented for each image data set. By way of example, it is also possible to use an interpolation or model-based reconstruction to determine position data for image data sets for which no position has been measured. The precondition for this is that the dynamics of the movement do not exceed the bandwidth of the position detection, which is limited by the discrete detection, or, should this nevertheless be exceeded, this overshoot is known to the system. Thus, in the case of a high-frequency vibration overlaid on the manual movement, where both the amplitude and the orientation of the vibration is known, it is sufficient to measure the position only once per vibration period in each case, for example at each zero crossing. Then, the positions adopted during a vibration period can be calculated on the basis of the known vibration.

Moreover, what is known as sensor fusion or information fusion can be used to detect the position; in this case, information items originating from different sensors are linked with one another. For example, a high-frequency but inaccurate inertial sensor system may be combined with a low-frequency but accurate tracking system. In this way, the less accurate position data and optional orientation data acquired by means of the inertial sensor system are recurrently calibrated using the accurate position data and optional orientation data of the tracking system before the inaccuracies potentially become too large.

In an advantageous development of the microinstrument system according to the invention, the microinstrument comprises a device for inducing a transverse vibration of the distal end of the at least one optical fiber or of the distal end of the microinstrument. By way of example, the device for inducing a transverse vibration may comprise at least one piezo element and a suitable controller for the at least one piezo element.

A line of image information in the vibration direction can be recorded as a result of the transverse vibration of the distal end of the at least one optical fiber or of the distal end of the microinstrument. If the sweeping direction of the distal end of the at least one optical fiber in that case does not extend parallel to the vibration direction, then, during the sweeping movement, even if only a single optical fiber is used for scanning, picture elements are recorded not only along a path corresponding to the sweeping movement, but along a strip which has an extent perpendicular to the line of the sweeping movement. This can be attained particularly advantageously if the device for inducing a vibration is designed such that it enables the induction of a transverse vibration with an adjustable orientation. By way of example, this can be achieved by using at least two piezo elements. In this configuration, the data processing device then is designed to determine the vibration-corrected movement direction of the distal end of the at least one optical fiber from temporally successive position data. It can then generate a control signal on the basis of the determined movement direction and output said control signal to the device for inducing a vibration, the control signal controlling the device in such a way that the transverse vibration is oriented perpendicular to the determined movement direction. In this way, the greatest possible extent of the scanned strip perpendicular to the movement direction can be obtained by way of the induced vibration.

In the microinstrument system according to the invention, the microinstrument may comprise a proximal end and a distal end, wherein the proximal end of the at least one optical fiber is located at the proximal end of the microinstrument and the distal end of the at least one optical fiber is located at the distal end of the microinstrument. A scanner can be present at the proximal end or at the distal end on the microinstrument and can be used to modify the direction of the light emerging from the corresponding end of the at least one optical fiber and of the light entering the corresponding end of the optical fiber. In this case, a scanner at the proximal end offers the advantage of requiring no installation space for the scanner at the distal end and the distal end therefore being able to be designed as small as possible. For example, in the case of a fiber bundle, a scanner at the proximal end can then be used to successively control each fiber bundle in a specific temporal sequence in order to acquire the image data. However, a scanner at the proximal end can also be used in the case of an individual optical fiber, specifically if the optical fiber has a refractive index gradient over its cross section. This leads to the exit direction of a light beam from one of the ends of the optical fiber depending on the entrance direction into the other end of the optical fiber. Consequently, a small region of the observation object can be scanned by a single fiber by way of a scanning movement at the proximal end, without this fiber needing to be moved relative to the observation object to this end.

A scanner at the distal end of the microinstrument particularly lends itself whenever the distal end of the microinstrument has movable parts in any case. By way of example, the at least one optical fiber can be integrated into the movable part of a vitrectome. This movable part carries out a longitudinal movement in the interior of a sleeve and serves to comminute the vitreous humor in the eye.

The invention also proposes a computer-implemented method for generating a two-dimensional or three-dimensional image of an observation object with the aid of a microinstrument which is part of a fiber-optic scanning system and in which an optical fiber with a distal end to face the observation object is integrated. The method comprises the following steps:

receiving or retrieving a plurality of image data acquired with the aid of the at least one optical fiber, said image data being acquired while the distal end of the at least one optical fiber is moved laterally over the region of interest of the observation object with the aid of the microinstrument. In this case, the image data may be individual picture elements, one- or two-dimensional images with a short length or a small area, or three-dimensional images with a small volume, as already mentioned above.

receiving or retrieving at least position data assigned to the image data, said position data representing the position of the distal end of the at least one optical fiber while the respective image data are acquired, or determining the position data from received or retrieved data, said data being assigned to the image data and allowing the position data of the distal end of the at least one optical fiber to be derived while the respective image data are acquired. By way of example, it is possible to determine by calculation the position data for the positions adopted by the distal end of the at least one optical fiber during a scan from received or retrieved orientation data, for instance if different positions of the distal end of the microinstrument are based on a rotation of the microinstrument about a point of rotation. In this case, the position of the distal end of the microinstrument can be determined on the basis of its orientation and the distance between the point of rotation and the distal end. Accordingly, the data from which the position data of the distal end of the at least one optical fiber can be derived can be orientation data. Stereoscopic image data also enter into consideration as data from which the position data of the distal end of the at least one optical fiber can be derived.

Especially if the orientation of the distal end of the at least one optical fiber changes with its position, it is moreover advantageous to receive or retrieve orientation data assigned to the image data in addition to the position data, said orientation data representing the orientation of the distal end of the at least one optical fiber when the respective image data are acquired during a scan, or to determine the orientation data from received or retrieved data assigned to the image data, from which data the orientation data of the distal end of the at least one optical fiber can be derived when the respective image data are acquired. By way of example, digital stereoscopic images can be data from which it is possible to derive orientation data.

The position data and/or the orientation data can directly specify the position and the orientation, respectively, of the distal end of the at least one optical fiber, or they can specify these indirectly, for example by virtue of the position and/or orientation of an element of the microinstrument, for instance a marker arranged on the microinstrument, being detected, with the position and/or the orientation of the distal end of the at least one optical fiber being known in relation to this element. Moreover, the position data and/or the orientation data can be absolute position data and absolute orientation data, respectively, which are given in a fixed coordinate system, or these can be relative position data and relative orientation data, respectively, which describe the position and orientation, respectively, of the distal end of the at least one optical fiber in relation to elements of the observation object or in relation to tissue structures extracted from previous images. The assignment of the position data and optionally the orientation data to the image data can be implemented, for example, on the basis of timestamps added to the position data and optionally the orientation data and also to the image data, the timestamps allowing the image data recorded at a time of the scan to be assigned the position data and optionally the orientation data collected or determined for this time. However, the assignment can also be implemented without timestamp, for example by virtue of image data acquired for a specific position and optionally orientation being stored in a common file with the position data and optionally orientation data collected or determined for these image data or, if all data are stored in a single file, by virtue of the image data acquired for a specific position and optionally orientation always being located immediately in front of or behind the associated position data and optionally orientation data in this file.

According to the invention, the two-dimensional or three-dimensional image is compiled with the aid of the position data and optionally the orientation data from image data acquired during the scan. In this way, a two-dimensional or three-dimensional image can be acquired using a single optical fiber, without the distal end of the at least one optical fiber needing to comprise a scanning device. If a fiber bundle with a plurality of optical fibers is integrated in the microinstrument, then two-dimensional or three-dimensional images with a greater extent can be compiled from the two-dimensional or three-dimensional images with a small extent as recorded by the fiber bundle. In this case, the computer-implemented method in particular allows the recording of an object region of interest by virtue of the user guiding the distal end of the fiber bundle or the distal end of the microinstrument over the object region of interest with a movement as if the intention were to paint the object region of interest. Image data are acquired at a multiplicity of positions during this movement and are then compiled to form an overall image with the aid of the position data, and optionally orientation data, likewise acquired for the individual positions.

If the utilized microinstrument comprises a scanner or a device for inducing a transverse vibration of its distal end or of the distal end of the at least one optical fiber, as described hereinabove, then the computer-implemented method may also contain a step of receiving or retrieving scanning data and/or vibration data. In this case, the vibration data may also be data from which the respective deflection of the distal end can be determined by calculation on the basis of a model of the vibration. If the vibration data for example represent the voltage supplied to a piezo element for the purpose of bringing about the vibration, then the respective deflection of the distal end can be determined by calculation on the basis of a model that reproduces the relationship between the voltage and the deflection. The scanning data and/or the vibration data can then also be taken into account when compiling the two-dimensional or three-dimensional image. For example, taking account scanning data may be advantageous if a fiber bundle is used to compile the image information collected by the individual optical fibers of the fiber bundle to form the small-area two-dimensional image acquired by the fiber bundle or the small-volume three-dimensional image. In the case of an individual optical fiber with a refractive index gradient, too, it is possible to acquire a two-dimensional or three-dimensional image with a small extent with the aid of knowledge about the respective scanner position, and hence the entrance and exit direction of the beam into the optical fiber and out of the optical fiber, respectively. In both cases, it is advantageous if the scanning speed is greater than the speed at which the distal end of the optical fibers or the distal end of the microinstrument is moved over the object region of interest. In this case, the scanning speed can be greater than the movement speed of the distal end of the optical fiber or of the distal end of the microinstrument by a factor of 10 to 1000. In particular, the scanning speed can be so high that the position of the distal end of the optical fiber or of the distal end of the microinstrument does not change substantially during a scan, which is to say that the change in position is no more than three times the distance between two adjacent picture elements in the scanned image, in particular no more than the single distance between two adjacent picture elements in the scanned image and preferably no more than half the distance between two adjacent picture elements in the scanned image. The scanned image contains no noticeable motion blur, especially if the change in position is no more than half the distance between two adjacent picture elements. If a little motion blur can be accepted for the intended use, then the change in position during a scan can also be greater than or equal to the single distance between two adjacent picture elements in the scanned image. However, it is also possible to take account of the lateral change in position of the distal end caused by the movement speed during an A-scan in the data of the A-scan. In other words, if the scanning speed is of the same order as the movement speed, or even slower, it is possible by way of making use of the position data to compile the image data, which are recorded at different depths and laterally shifted with respect to one another, with the correct position in the two-dimensional or three-dimensional image to be created.

According to a further aspect of the present invention, a method for recording a two-dimensional or three-dimensional image of a region of interest of an observation object by fiber-optic scanning is made available, with a microinstrument being used within the scope of the method and at least one optical fiber with a distal end to face the observation object being integrated in said microinstrument. The recording by fiber-optic scanning is implemented while the distal end of the at least one optical fiber is moved over the region of interest of the observation object with the aid of the microinstrument. In particular, the movement can be implemented manually and can be carried out as if the intention were to paint the region of interest of the observation object. The method comprises the following steps:

collecting position data for a number of positions on the path along which the distal end of the at least one optical fiber is moved during the movement over the region of interest of the observation object, or collecting data from which it is possible to derive the position data of the distal end of the at least one optical fiber when the respective image data are acquired and determining the position data from these data. As already mentioned hereinabove, it is possible to determine the position data by calculation from orientation data, from stereoscopic images, or from the image data themselves.

collecting image data and assigning the image data to the respective position data. To assign the position data to the image data, it is for example possible to synchronize the position data and the image data with one another in time.

compiling the image data to form the two-dimensional or three-dimensional image with the aid of the position data.

With the aid of the method according to the invention for recording a two-dimensional or three-dimensional image of a region of interest of an observation object by fiber-optic scanning, a surgeon is able to intraoperatively image a freely selectable object region of interest in two dimensions or three dimensions by virtue of guiding the distal end of the at least one optical fiber or the distal end of the microinstrument over the region of interest in a sweeping movement for the purpose of performing a scan. This method for acquiring two-dimensional or three-dimensional images can be carried out intuitively and does not require a complex configuration of the distal end of the microinstrument. In particular, since a single optical fiber is enough to carry out the method, microinstruments with a very small diameter can be used to this end, with the result that the method can in particular also be applied without problems in eye surgery and neurosurgery.

Especially if the orientation of the distal end of the at least one optical fiber can change with its position, it is moreover advantageous if, in addition to the position data, orientation data for the number of positions on the path along which the distal end of the at least one optical fiber is moved during the movement over the region of interest of the observation object are collected, or the orientation data are determined from collected data from which it is possible to derive orientation data for the number of positions on the path along which the distal end of the at least one optical fiber is moved during the movement over the region of interest of the observation object. In addition to the respective position data, the image data can then also be assigned to the respective orientation data, and compiling the image data acquired by the scan to form the two-dimensional or three-dimensional image can be implemented not only with the aid of the position data but also with the aid of the orientation data. To enable an assignment of the collected or determined position data and orientation data to the image data collected during a scan, it is possible to record firstly the orientation data and secondly the image data, for example in a manner synchronized with one another in time, and provide these with timestamps or store these in an order signifying the association of the image data with simultaneously recorded orientation data.

If it is not only a single optical fiber that is integrated in the microinstrument but a plurality of optical fibers whose positions relative to one another are known, for example as is the case in an optical fiber bundle, then a two-dimensional or three-dimensional image can be recorded at each position of the sweeping movement, the lateral dimensions of said image being determined by the lateral extent of the arrangement of optical fibers. This makes it possible to increase the distances between points at which the two-dimensional or three-dimensional images with small dimensions are recorded, in comparison with the points required in the case of a single optical fiber. Then again, it is also possible to maintain the same distances as in the case of a single optical fiber, whereby the recorded two-dimensional or three-dimensional images with small dimensions overlap one another. In this way, redundant picture elements arise during a scan and these increase the signal intensity of the respective picture elements and consequently improve the signal-to-noise ratio. Moreover, it is possible to increase the resolution if, in the case of overlapping images, the object regions are shifted relative to one another by an absolute value which is below the resolution of the individual images. The picture elements of the respective images represent intensity values of the light reflected by the object, with the intensity values in the individual images being arranged in a grid in which the distance between the grid points corresponds to the image resolution. By a shift by an absolute value smaller than the pitch of the grid points, it is possible to determine an intensity value located between the grid points of the images from the intensity values of the images, and it is possible to synthesize an image, in which the grid pitch between the individual intensity values is reduced, whereby the synthesized image has a higher image resolution than the images from which it has been obtained. At this point, reference is made to the fact that the distances between the positions at which image data are recorded can be adjusted by setting a suitable frequency at which image data are recorded and position data are collected.

It should also be mentioned that there is the option of triggering the collection of the image data by the position data. By way of example, it is possible to specify a position grid and, whenever a position on the position grid is reached, image data are collected for this position, or it is possible to specify a specific shift, after which a new collection of image data is implemented. However, it is alternatively also possible to trigger the collection of position data by the collection of image data, which is to say each instance of image data being recorded is accompanied by the collection or determination of position data and optionally orientation data for the location of the recording. However, it is not important within the scope of the invention what is triggered by what, but rather that, firstly, the collected image data and, secondly, the collected or determined position data and optionally orientation data can be uniquely assigned to one another. By way of example, the assignment can be implemented by means of a temporal synchronization, for instance with the aid of timestamps in the image data and the position data and optionally the orientation data, or the assignment can be implemented by a specific sequence of storing the data. By way of example, the image data and the associated position data and optionally orientation data can be stored in a single file, with data representing a position and optionally an orientation always being stored immediately before or after the image data belonging to this position and optionally orientation.

Within the scope of the invention there is also the option of inducing a transverse vibration of the distal end of the at least one optical fiber or of the distal end of the microinstrument, with the position data and optionally orientation data being captured at different positions of the distal end of the at least one optical fiber during a vibration period of the induced vibration. In this way, the region swept over when sweeping over the region of interest of the observation object along the path can be increased. This especially applies if the current direction of the path along which the distal end of the at least one optical fiber is moved during the movement over the region of interest of the observation object is determined and, as the transverse vibration of the at least one distal end of the at least one optical fiber or distal end of the microinstrument, a transverse vibration running perpendicular to the determined current direction is induced. In this way, it is possible to sweep over a broad region along the path during the movement, in particular a maximally broad region.

In this configuration of the method there is, as a matter of principle, the option of the position detection and optionally the orientation detection being implemented so fast that individual positions and optionally individual orientations can be resolved during a vibration period of the transverse vibration. Then again, if the amplitude, the frequency and the vibration direction of the vibration are known, it is sufficient to carry out the collection of the position data and optionally the orientation data at a frequency which corresponds to a vibration period and to determine the individual positions and optionally orientations of the distal end of the at least one optical fiber or of the distal end of the microinstrument with the aid of the vibration frequency and the vibration amplitude, using the detected position as a starting point. However, the recording frequency with which the image data are recorded must then at least equal the frequency of the vibration so that a plurality of image data can be acquired during one vibration period.

In a further development of the method according to the invention, there is the option of modifying the direction of the light supplied to the distal end of the at least one optical fiber for the purpose of recording the image data while the distal end of the at least one optical fiber or the microinstrument is moved over the region of interest of the observation object. By way of example, this can be implemented with the aid of a scanner at the distal end of the at least one optical fiber or of the microinstrument, or by virtue of the fact that an optical fiber with a refractive index gradient is used, at the proximal end of which a scanner is present and used to steer light emerging from the optical fiber from different directions onto a light-sensitive sensor of the recording apparatus. In the just-described modification of the method according to the invention, the scanner used at the proximal end or at the distal end of the at least one optical fiber or of the microinstrument should have a scanning frequency that is so high that the position and the orientation of the distal end of the at least one optical fiber or of the distal end of the microinstrument do not change substantially during a scan, as has already been described hereinabove.

Further features, properties and advantages of the present invention will become apparent from the following description of exemplary embodiments with reference to the accompanying figures.

Figure 1:
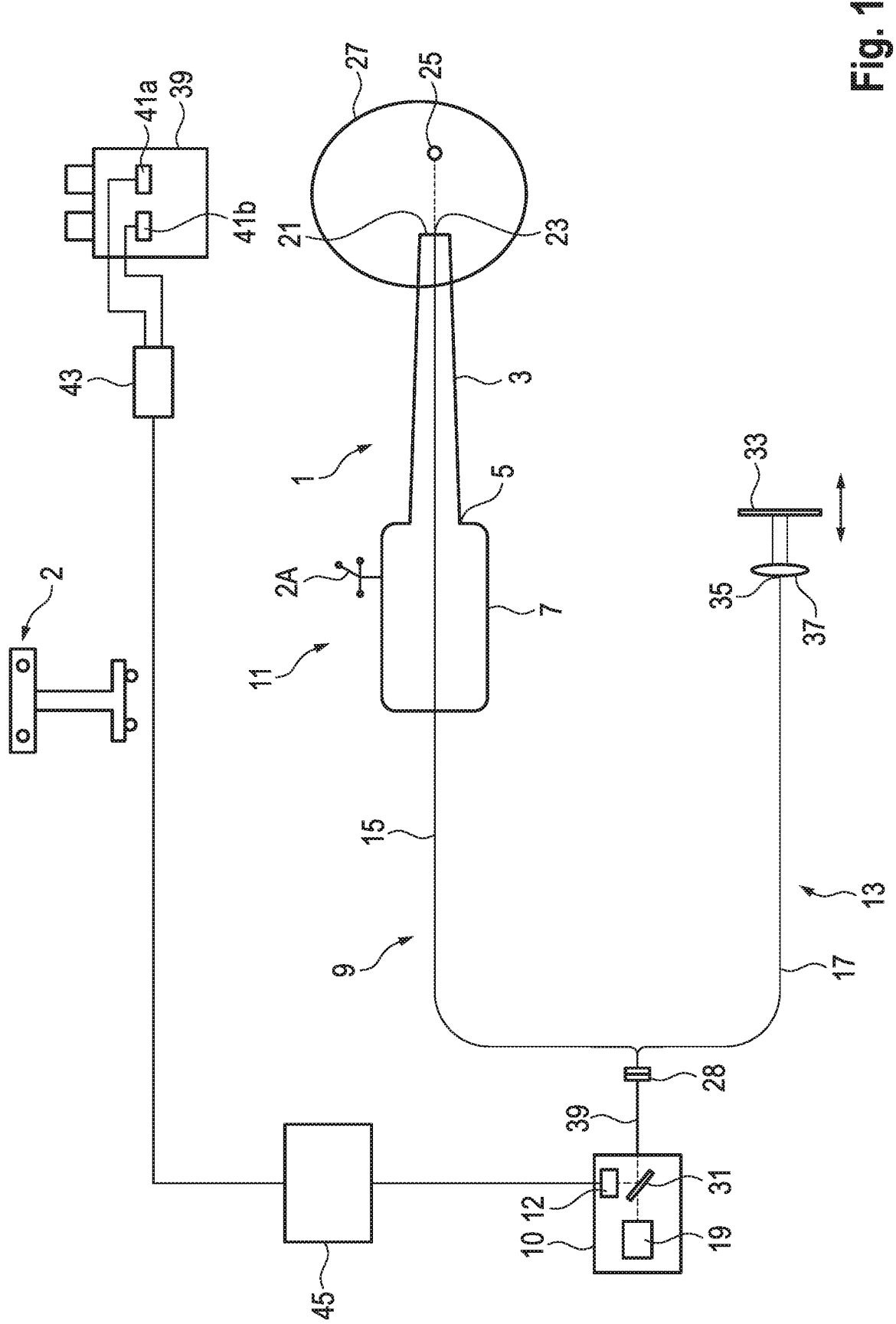
FIG. 1 shows a first exemplary embodiment of a microinstrument system.

A first exemplary embodiment of the microinstrument system according to the invention is described hereinafter with reference to FIGS. 1 to 11.

The microinstrument system of the first exemplary embodiment comprises a microinstrument 1, which is in the form of a probe. The latter comprises a cannula 3 or another rod-like or tubular structure, which has an external diameter of 1.5 mm or less, preferably 1.0 mm or less, and in particular 0.6 mm or less, in the present exemplary embodiment. A handle 7 allowing a treating surgeon to guide the microinstrument 1 is located at the proximal end 5 of the cannula 3.

The microinstrument system also comprises a recording apparatus which is in the form of an OCT system 9 in the present exemplary embodiment. An OCT system can be used to record image data from different object depths of an observation object 27. To this end, illumination light is split into an object branch 11 and a reference branch 13. Both the object branch 11 and the reference branch 13 each comprise an optical fiber 15 and 17, respectively, into which light from an illumination device, a laser 19 integrated in OCT hardware 10 in the present exemplary embodiment, is input coupled via a fiber portion 25 common to both the object branch 11 and the reference branch 13 and via a coupler 28 arranged at the distal end thereof. The optical fiber 15 of the object branch extends through the microinstrument 1 to the distal end 21 of the cannula 3, where the distal end 23 of the optical fiber 15 of the object branch 11 is located. A collimation optical unit, with the aid of which a parallel beam is directed at a mirror 33 and with the aid of which the parallel beam reflected by the mirror 33 is focused at the distal end 35 of the optical fiber 17 of the reference branch 13, is located at the distal end 35 of the optical fiber 17 of the reference branch 13. The optical fibers 15, 17 of the object branch 11 and reference branch 13 have the same optical length, and the mirror 33 has a distance from the distal end of the optical fiber 17 of the reference branch 13 which substantially corresponds to the distance of the distal end 23 of the optical fiber 15 of the object branch 11 from the observation object 27.

The light emerging from the distal end 23 of the optical fiber 15 of the object branch 11 illuminates the observation object 27, which can be for example a portion or structure in the interior of the eye or a neural structure, for example within the brain. To this end, a micro-optical unit or a lens based on a refractive index gradient (not depicted here) is present at the distal end 23 of the optical fiber 15 and focuses light at a point 25 of the observation object 27. In this case, the monochromatic laser light penetrates into the tissue of the observation object 27 to a certain depth. The laser light is reflected from the entire depth range into which it penetrates. Then, the reflected laser light is input coupled into the distal end 23 of the optical fiber 15 again by means of the micro-optical unit or the lens based on the refractive index gradient and is guided to the coupler 28, which then input couples said light into the common fiber portion 25. Then, via a beam splitter 31 which is arranged in the OCT hardware and which may be designed as a beam splitter mirror or beam splitter prism, for example, the light is supplied from the common fiber portion 25 to a detector 12 which is likewise arranged in the OCT hardware.

In addition to the light from the object branch 11, light from the reference branch 13 is also input coupled into the common fiber portion 29. The mirror 33, whose distance from the common fiber portion 29 can be varied, was previously illuminated by the input coupled light. The distances of the mirror 33 from the distal end of the optical fiber 17 of the reference branch 13 which arise during this variation correspond to the distances between the depth regions in the object 27, from which the laser light is reflected, and the distal end 23 of the optical fiber 15 of the optical branch 11. The optical path length which the light travels in the reference branch can be varied by shifting the mirror 31 relative to the distal end 35 of the optical fiber 17 of the reference branch 13. If the optical path length of the light reflected by the mirror 33 corresponds to the optical path length of the light reflected from a certain depth of the observation object 27, then there is a constructive superposition in the common fiber portion 29 of the light from the reference branch 13 and the light from the object branch 11. This leads to an increase in intensity at the detector, which in turn leads to the constructively interfering light forming the majority of the detected light. In this case, the distance of the mirror 31 from the distal end 35 of the optical fiber 17 in the reference branch 13 determines the depth in the observation object 27 from which the light has to be reflected in order to be able to constructively interfere with the light in the reference branch 13. If the distance of the mirror 31 from the distal end 35 of the optical fiber 17 of the reference branch 13 is now moved, then this leads during the movement to the light from different depths of the observation object 27 constructively interfering with the light of the reference branch 13, depending on the mirror setting, with the result that the movement of the mirror over this given range enables a scan of a given depth range in the observation object 27. Such a scan over a certain depth range is referred to as depth scan or A-scan.

At this point, attention is drawn to the fact that other forms of OCT systems are also possible, especially also those that make do with a stationary mirror 33. By way of example, all depth ranges of the object can be recorded simultaneously with the aid of white-light interferometry. What is exploited in this case is that white light comprises a multiplicity of wavelengths, which, for a fixed optical path length in the reference branch 13, leads to the constructive interference for each wavelength in the white light occurring at a slightly different optical path length in and of the object branch 11. Thus, in the case of a fixedly arranged mirror, the condition for constructive interference at a specific wavelength is determined by the depth of the observation object 27 from where the reflection is implemented. By contrast, other wavelengths satisfy the condition for constructive interference at different depths in the observation object, with the result that the depth information is encoded in the spectral distribution of the light detected by the detector.

The microinstrument system also comprises a determination device for determining the position and, if necessary, the orientation of the microinstrument 1. In the present exemplary embodiment, a tracking system 2 serves as a determination device which, on the basis of a marker 2A arranged on the microinstrument 1, detects the position and, if necessary, the orientation of the microinstrument 1 and which determines the position and the orientation of the distal end of the cannula 3 on the basis of the known arrangement of the marker 2A relative to the distal end of the cannula 3. Alternatively, the detection device may comprise an inertial sensor system or a surgical microscope 39 with two stereoscopic component beam paths that each have a digital image sensor 41A, 41B. The images recorded by the two image sensors 41A, 41B are then supplied to an evaluation unit 43 which, with the aid of image processing software, recognizes the distal end of the cannula 3 in the recorded images and, on the basis of stereoscopic information, determines the position and optionally the orientation of the distal end 21 in relation to the observation object or in relation to the coordinate system of the surgical microscope.

The image data recorded by the detector 12 in the OCT hardware 10 are output, together with the position data determined by the evaluation unit 43 and the optionally determined orientation data, to a data processing apparatus 45, a commercially available PC in the present exemplary embodiment, to which the evaluation device 43 of the determination device and the detector 12 of the OCT hardware 10 are connected. However, alternatively, the data processing apparatus 45 may also be a dedicated hardware component. Software is installed on the computer 45 and compiles the image data acquired with the OCT system to form a two-dimensional or three-dimensional image with the aid of the position data and optionally the orientation data. To this end, the respectively recorded image data and the respectively collected position data and optionally orientation data are provided with timestamps in the present exemplary embodiments, on the basis of which timestamps the image data can be assigned to a detected position and optionally to a detected orientation.

Recording two-dimensional or three-dimensional images with the aid of the above-described microinstrument system is described hereinbelow with reference to FIGS. 2 to 11.

Recording a two-dimensional or three-dimensional image by fiber-optic scanning with the aid of the microinstrument system shown in FIG. 1 is described below with reference to FIGS. 2 and 3. In this case, FIG. 2 shows the movement of the microinstrument 1 in a side view and FIG. 3 shows an example of the path of the movement in a plan view.

Figure 2:
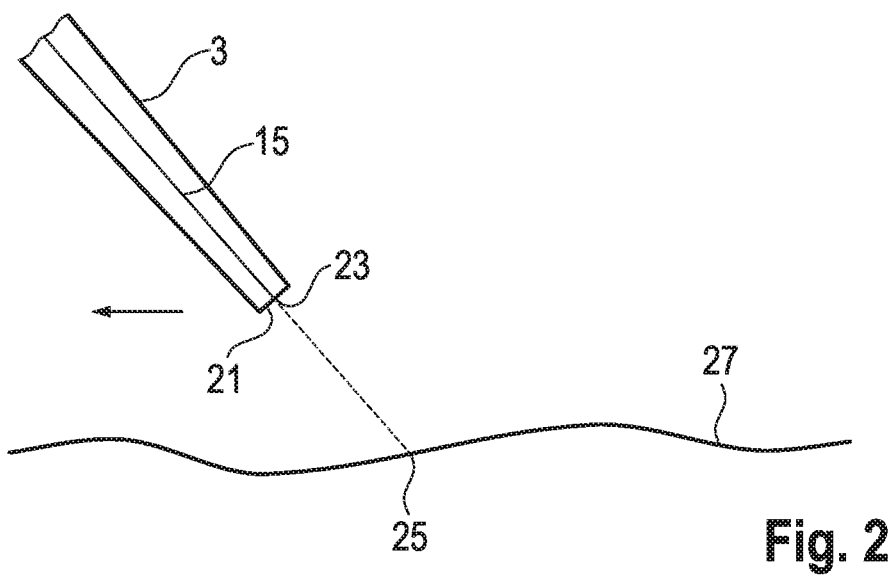
FIG. 2 shows a schematic illustration of the movement of the distal end of a microinstrument within the scope of the method for recording a two-dimensional or three-dimensional image in a side view.
Figure 3:
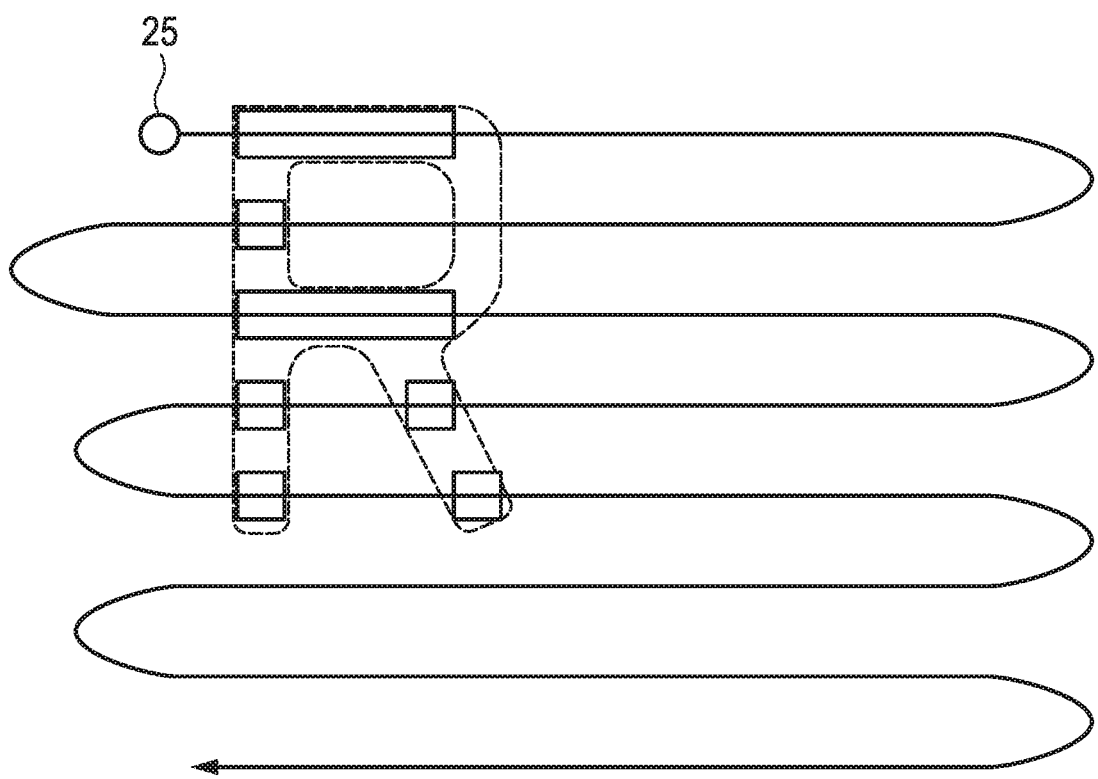
FIG. 3 shows the path of the distal end of the microinstrument when recording a two-dimensional or three-dimensional image in a plan view.

To record a two-dimensional or three-dimensional image, the distal end 21 of the microinstrument 1 is moved laterally over the surface of the observation object 27, as indicated by the arrow in FIG. 2, for the purpose of performing a scan. If the intention is to record a two-dimensional image, the distal end 21 of the microinstrument 1 need only be guided along a line over the surface, as if the intention were to paint a line onto the observation object. Then, A-scans are recorded along the line with the aid of the OCT system and, with the aid of the position data and optionally the orientation data, can be compiled to form a two-dimensional image in which the one dimension represents the line and the second dimension is the depth within the observation object from where the light has been reflected. Such a two-dimensional image is also referred to as a B-scan. In order to generate a three-dimensional image, the distal end 21 of the microinstrument 1 must be moved over the entire region of interest for the purpose of performing a scan, as depicted on the basis of the exemplary path in FIG. 3. This path represents a type of back-and-forth movement of the distal end 21 of the microinstrument, as if the intention were to paint the region of interest. Image data are recorded at a multiplicity of positions along the path of the distal end 21 of the microinstrument 1. Moreover, the associated position data and optionally the associated orientation data of the distal end 21 are determined for all captured image data and are assigned to the respective image data. In the present exemplary embodiment, the position data and optionally the orientation data are assigned to the respective image data on the basis of the timestamp. However, this may for example also be implemented by virtue of the image data, the position data, and optionally the orientation data being written to a common file, in which the position data and optionally orientation data assigned to the image data always immediately precede the image data or always immediately follow the image data.

Compiling the image data with the aid of the position data and optionally orientation data assigned thereto is then implemented with the software installed on the computer 45, the software executing the following steps of a computer-implemented method:

(i) receiving or retrieving the image data acquired by the OCT system, which represent A-scans acquired with the aid of the OCT system in the present exemplary embodiment, and also the position data assigned to the image data and, if necessary, the orientation data assigned to the image data.

(ii) determining the positions and optionally the orientations of the A-scans relative to one another on the basis of the position data assigned to the image data and optionally the orientation data assigned to the image data, and (iii) constructing the two-dimensional or three-dimensional image by compiling the A-scans which are correctly positioned with respect to one another and, if necessary, correctly oriented with respect to one another, wherein there also is the option of interpolating between the individual picture elements of the two-dimensional or three-dimensional image.

Rather than determining the positions and optionally the orientations of the A-scans relative to one another, it is alternatively also possible to determine the positions and optionally the orientations of the A-scans in a fixed coordinate system, wherein the A-scans are then positioned at the corresponding positions of the coordinate system and optionally in the corresponding orientations for the purpose of constructing the two-dimensional or three-dimensional image.

Even though FIG. 2 shows a path for the movement of the distal end 21 of the microinstrument 1, in which linear path sections extend adjacently to one another, any other desired path which can be used to cover the region of interest is also suitable as a matter of principle. By way of example, the region of interest could be swept over with a spiral movement starting from a central point. However, even a fully arbitrary, irregular movement over the region of interest leads to a result since the individual A-scans can be compiled to form a three-dimensional image in any case on the basis of the assigned position data and optionally the assigned orientation data.

A modification of the exemplary embodiment shown in FIG. 1 is described hereinbelow with reference to FIGS. 4 and 5. In this modification, the microinstrument 1 comprises two piezo elements which can be used to make the cannula 3 vibrate. The piezo elements are arranged distributed at an angle of 90 degrees about the axis of the cannula such that the piezo elements 47, 49 can be used to introduce mutually perpendicular transverse vibrations into the cannula. By suitably controlling the piezo elements 47, 49, the transverse vibrations can be induced along any desired radial direction of the cannula 3.

In the described modification, the computer 45 determines the current movement direction and movement speed of the distal end 21 of the microinstrument 1 over the region of interest of the observation object on the basis of the collected position data and optionally the orientation data. This current movement direction is depicted in FIG. 5 on the basis of the movement direction of the spot 25 on the observation object, at which an A-scan is recorded. The movement direction is represented by the arrow starting from the point 25. The computer 45 then determines the direction perpendicular to the movement direction determined in advance and drives the piezo elements 47, 49 such that they induce a linear vibration perpendicular to the current movement direction. Since the vibration data are known, this vibration can be removed from the collected position data and optionally the collected orientation data by calculation when the movement direction of the distal end 21 of the microinstrument 1 is determined.

Figure 4:
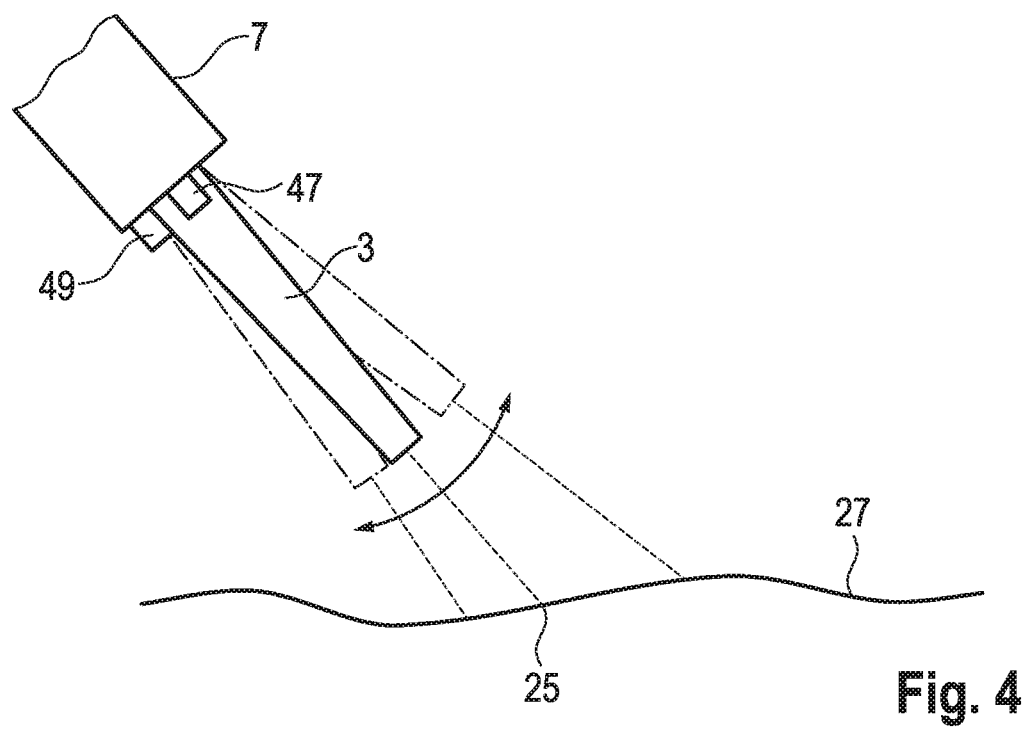
FIG. 4 shows a modification of the first exemplary embodiment, in which the distal end of the microinstrument is made to vibrate, in a side view.
Figure 5:
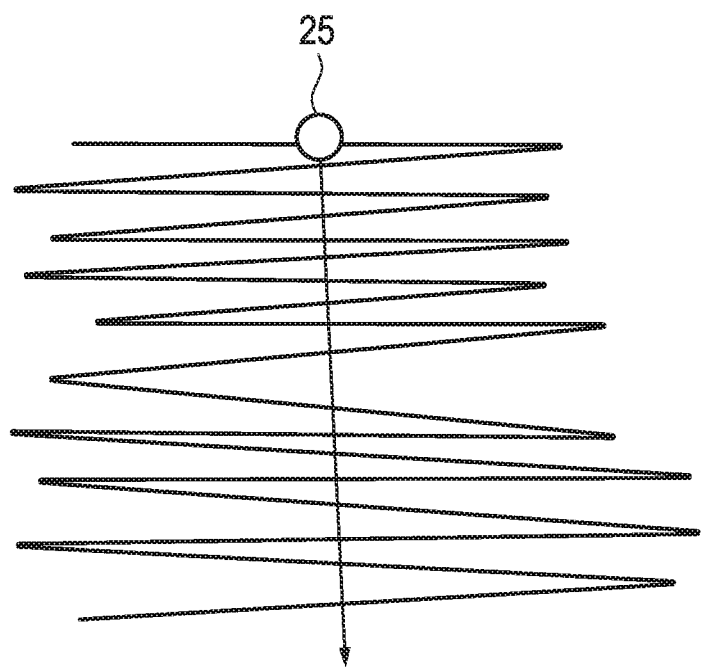
FIG. 5 shows the movement direction of the distal end of the microinstrument according to FIG. 4, together with the vibration superimposed on the movement direction.

In the modification of the microinstrument system shown in FIGS. 4 and 5, the images are recorded so quickly that a plurality of images are recorded during one vibration period. In this context, the vibration is generally used at a frequency which is so high that the zero position of the vibration does not substantially change its position perpendicular to the vibration direction during one vibration period. Since the microinstrument is guided by hand for the purpose of scanning the region of interest, it may however be the case that, on account of an irregular manual movement speed, there is a relatively large change in the zero position during one vibration period, for instance as shown in the center of FIG. 5. However, since the computer not only knows the vibration frequency and the vibration amplitude but also detects the movement speed perpendicular to the vibration direction, speed fluctuations occurring during the scan can be taken into account when compiling the three-dimensional image.

With the aid of the vibrating distal end 21 of the cannula 3, it becomes possible to record a three-dimensional image without a manually guided back-and-forth movement, as shown in FIG. 3, being required. All that is required is a movement along a line. If there nevertheless is a back-and-forth movement, the vibrating distal end 21 of the cannula 3 allows the distances between adjacent regions of the path to be increased, as for example is also possible when painting with a wide brush. In this way, a region of the observation object with a large area can be quickly supplied to three-dimensional imaging.

Figure 6:
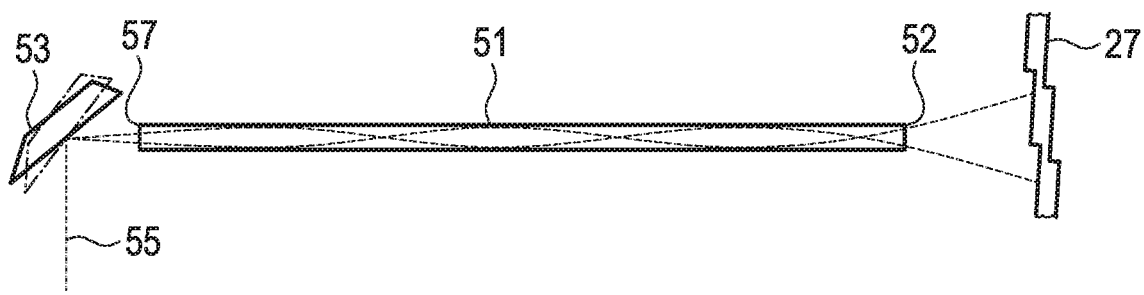
FIG. 6 shows a further modification of the first exemplary embodiment in a schematic illustration.

Even though the whole cannula 3 has been made to vibrate in the described modification of the first exemplary embodiment, there is also the option of only making the optical fiber 15 in the interior of the cannula 3 vibrate. Moreover, there is the option of causing a vibration of the object light beam of the OCT system without requiring a mechanical vibration of the cannula 3 or of the optical fiber 15 in the reference branch 11. This is made possible if use is made of an optical fiber 51 with an index gradient perpendicular to the longitudinal direction of the optical fiber 51. Then, the exit direction of the object light beam from the distal end 52 of the optical fiber 51 depends on the entrance direction of the light into the optical fiber 51. If the light is now input coupled into the proximal end 57 of the optical fiber 51 in different directions, for example by using a vibrating galvanometer mirror, then this leads to the exit direction of the light emerging from the distal end 52 of the optical fiber 51 changing its exit direction with the vibration of the galvanometer mirror 53. The same applies to the entrance direction of the light reflected by the observation object 27, which is then transmitted by the galvanometer mirror in the direction of the detector 12. Thus, with the aid of the vibration, it is thereby possible to record not only image data along the path along which the microinstrument 1 is guided by hand, but also image data from a region to the left and right of this path. An optical fiber 51 with an index gradient and a vibrating galvanometer mirror 53 arranged at its proximal end 57 is depicted in FIG. 6. Moreover, the course of an object light beam 55 input coupled into the optical fiber 51 is plotted schematically as far as the observation object 27.

In principle, it is moreover possible to exploit the fact that a hand-guided movement always also includes a tremor. This tremor can be considered to be like a vibration of the distal end of the microinstrument and can likewise be used to record image data from a region to the left and right of the hand-guided path over the observation object 27. Since the amplitude, the frequency, and the direction of the vibration resulting from the tremor are not known in this case, the frequency at which the position detection and optionally the orientation detection of the distal end 21 of the microinstrument 1 or of the distal end 23 of the optical fiber 15 is implemented should be so high that the fluctuating recording positions on account of the tremor are able to each be detected on an individual basis when recording the image data. In the case of an induced vibration whose amplitude, frequency, and direction are known, it is sufficient for the frequency at which the position data and optionally the orientation data are collected to be high enough to determine the respective zeros of the individual vibration periods. The individual recording positions when recording the image data during a vibration period can then be determined on the basis of the frequency, the amplitude, and the direction of the vibration proceeding from the zero position. Although the captured zero position will fluctuate around the path of the hand-guided movement, this fluctuation can be corrected on the basis of the known frequency, the known amplitude, and the known direction of the vibration. The corrected position then represents the zero position.

Figure 7:
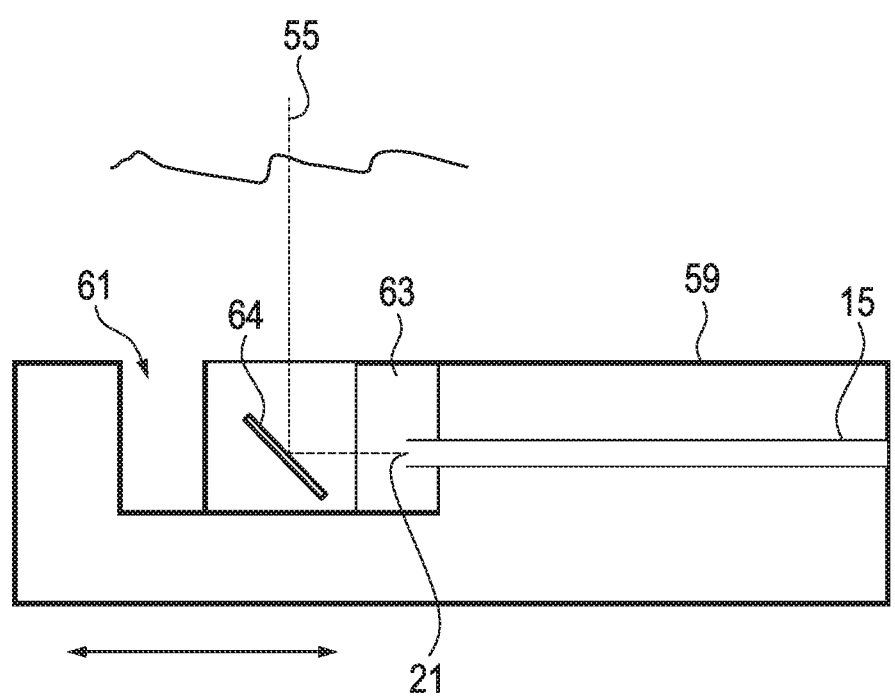
FIG. 7 shows the distal end of a microinstrument, as can be used within the scope of the first exemplary embodiment.

A further option for superimposing a second direction on the movement direction of the hand-guided microinstrument 1 consists of arranging a movable scanner at the distal end of the microinstrument. Such a variant of the first exemplary embodiment is schematically depicted in FIG. 7. In this variant, the microinstrument 1 is not only a simple cannula through which the optical fiber 15 of the object branch 11 is guided. Instead, the microinstrument is embodied as a vitrectome for comminuting the vitreous humor of the eye. Such a vitrectome comprises a hollow shaft 59 with an opening 61. A likewise hollow tube 63 which is movable in its longitudinal direction is arranged in the hollow shaft 59. Comminuted vitreous humor pieces are aspirated through this hollow tube 63. In the process, the hollow tube moves longitudinally back and forth between a position in which the opening 61 is fully sealed by the tube and a position in which the opening is open. If, as depicted schematically in FIG. 7, the distal end of the tube 63 is now provided with a reflective element, for example a mirror or a prism, its back-and-forth movement can be used to scan a region of the observation object 27 with the object light beam 55, the region substantially corresponding to the path traveled by the tube 63 during the back-and-forth movement. In contrast to the previously described embodiment variants of the first exemplary embodiment, the image data are recorded not in the longitudinal direction of the optical fiber 15 but in the radial direction with respect to the optical fiber 15 in the embodiment variant shown in FIG. 7.

Figure 8:
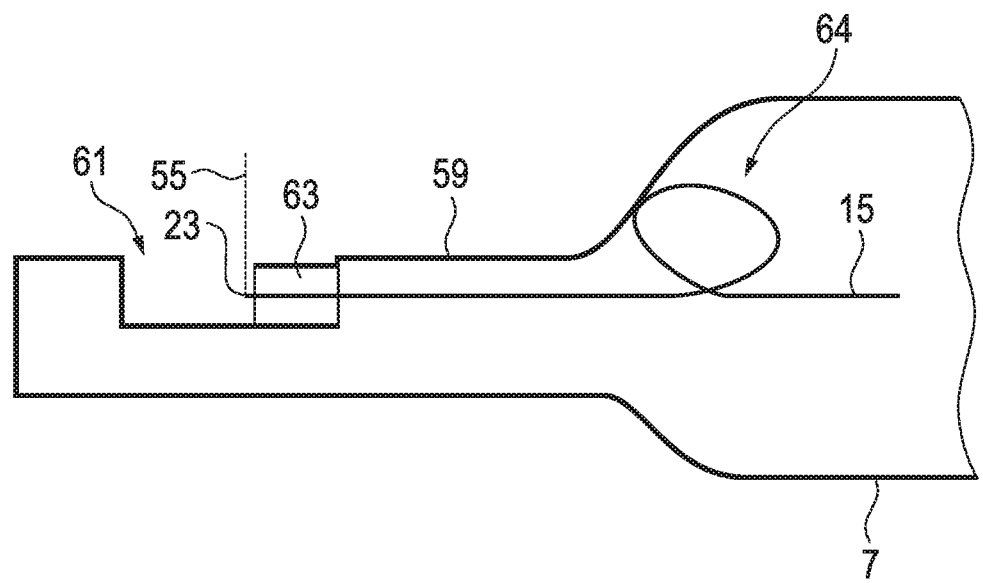
FIG. 8 shows an alternative configuration of the distal end of the microinstrument, as can be used within the scope of the first exemplary embodiment.

While the optical fiber 15 itself is stationary, which is to say it is not moved, in the embodiment variant shown in FIG. 7, there is likewise the option of also moving the optical fiber with the inner tube 63. To this end, an elastic part of the optical fiber 15 may be present, for example in the handle 7 of the vitrectome. For example, as depicted in FIG. 8, this elastic part can be realized by a loop which becomes tighter or looser with the movement of the inner tube 63. Moreover, the distal end 23 of the optical fiber 15 comprises a deflector (not depicted in FIG. 8) in this embodiment variant, said deflector deflecting the object light beam in the radial direction of the optical fiber 15 upon exit from the optical fiber 15.

The configuration shown in FIG. 8 for scanning the object offers the advantage over the embodiment variant shown in FIG. 7 that the optical path length in the object path 11 does not change by the back-and-forth movement of the inner tube 63. By contrast, in the variant shown in FIG. 7, the travel of the back-and-forth movement of the reflective element 64 leads to a change in the optical path length in the object branch 11, which must be compensated for by adapting the optical path length in the reference branch 13. This adaptation can be implemented mechanically, for example by virtue of shifting a zero position of the moving mirror 33 in the reference branch 13 with the position of the reflective element 64 during the back-and-forth movement in the object branch 15, or electronically, by virtue of the change in the path length in the object branch 11 being accounted for by the computer 45, for example in order to correct the object depths, at which the individual constructively interfering wavelengths have been reflected, on the basis of the respective position of the reflective element 64 during its movement. If it is not an OCT system but for example a confocal laser scanning microscope that is used to acquire the image data, there is the option of providing the system with such a great focal depth that the travel of the reflective element 64 during the back-and-forth movement does not substantially impair the focusing.

Figure 9:
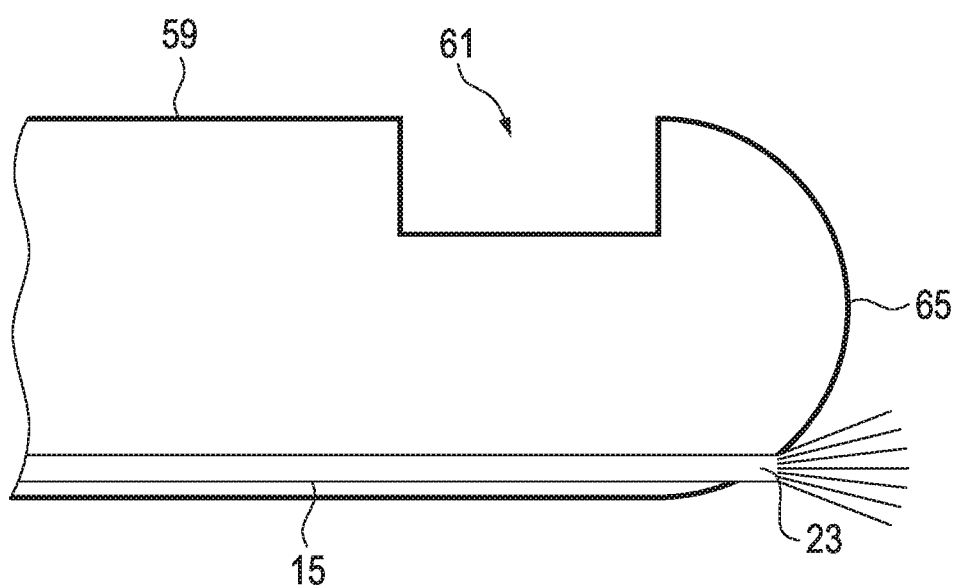
FIG. 9 shows a further alternative configuration of the distal end of the microinstrument, as can be used within the scope of the first exemplary embodiment.
Figure 10:
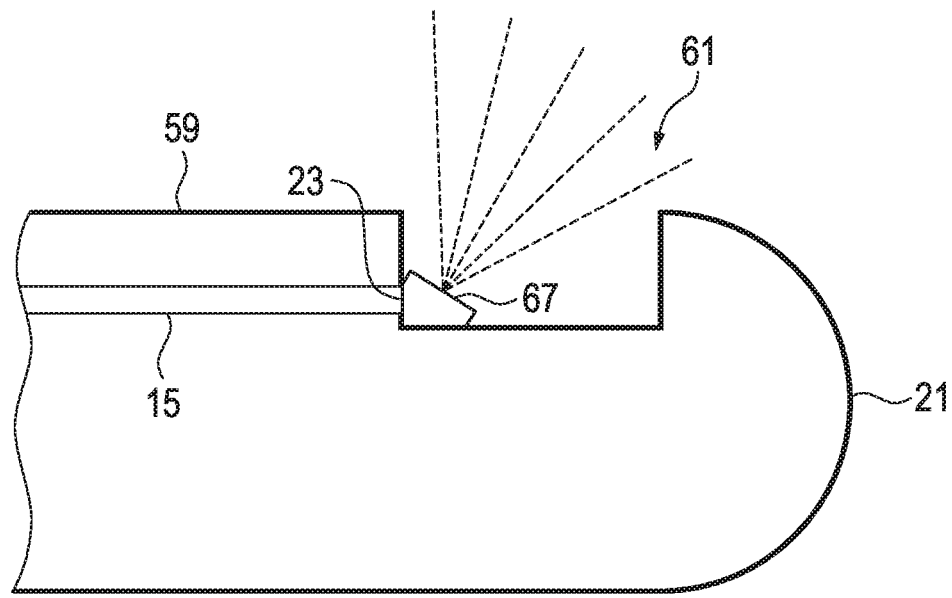
FIG. 10 shows yet a further modification of the distal end of the microinstrument, as can be used within the scope of the first exemplary embodiment.

The vitrectomes described with reference to FIGS. 7 and 8 allow image data to be recorded in the radial direction of the optical fiber 15 of the reference branch 11. However, there is also the option of using the vitrectome like the above-described cannula. In this case, the optical fiber 15 of the object branch 11 is guided up to the distal end 65 of the shaft such that the distal end 23 of the optical fiber 15 terminates flush with the distal end 65 of the vitrectome, as shown in FIG. 9.

However, there is also the option of recording the image in other directions to the longitudinal direction of the optical fiber 15 or the radial direction of the optical fiber 15. To this end, a deflector 67 which deflects the object light beam emerging from the distal end 23 of the optical fiber 15 in a direction located between the longitudinal direction and the radial direction of the optical fiber 15 (see FIG. 10) may be arranged at the distal end of the optical fiber 15 of the object branch 11. By way of example, the deflector can be designed as a microprism or as what is known as an "off axis freeform TIR mirror". In an "off axis freeform TIR mirror", the deflection is implemented on account of total-internal reflection (TIR), with the reflection direction being determined by the shape of a freeform surface. A plurality of possible alternative directions in which images can be recorded are schematically depicted in the figure.

Figure 11:
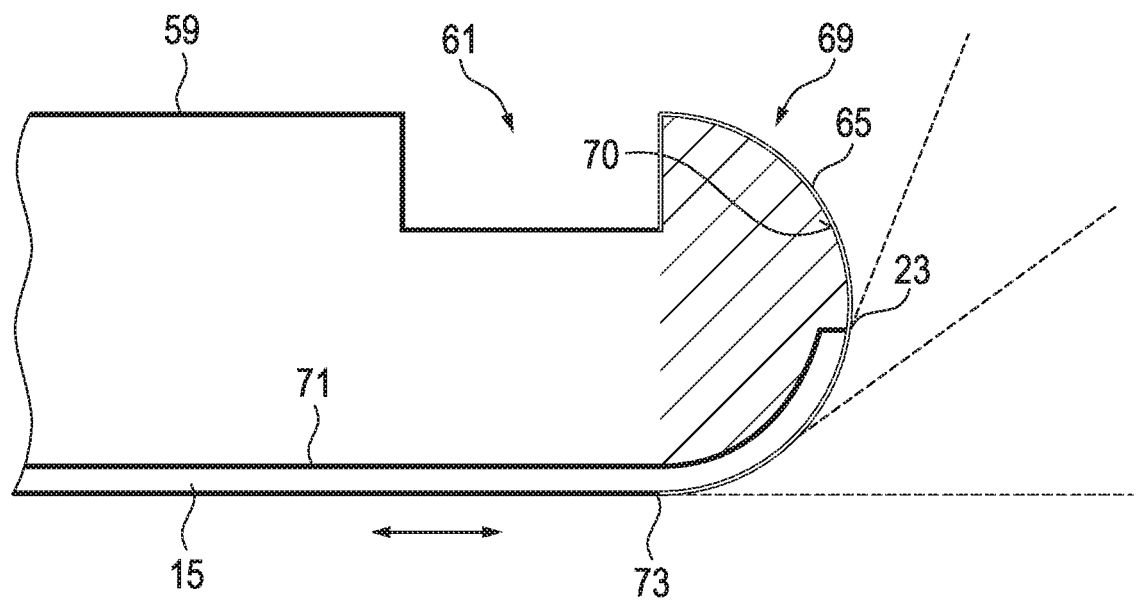
FIG. 11 shows yet a further modification of the distal end of the microinstrument, as can be used within the scope of the first exemplary embodiment.

Yet a further variant of the first exemplary embodiment is depicted in FIG. 11. In this embodiment variant, the distal end 65 of the shaft of the vitrectome is formed as a transparent region 69. This transparent region 69 substantially has the shape of a hemispherical shell with a hemispherical inner surface 70. A guide rail 71 extending up into the transparent region 69 is present in the interior of the shaft 59, and the distal end 23 of the optical fiber 15 of the object branch 11 can be moved longitudinally between the guide rail 71 and the wall 73 of the transparent region 69 with the aid of said guide rail. As a result of this longitudinal movement it is possible to set the position of the distal end 21 of the optical fiber 15 along the hemispherical inner surface 70, along with the orientation of said fiber, wherein the orientation and hence the emission direction of the optical fiber depends on the position of the distal end 21 at the inner surface 70 of the transparent region 69. This allows the emission direction of the object light or the recording direction when recording the image data to be varied, as depicted in FIG. 11.

Figure 12:
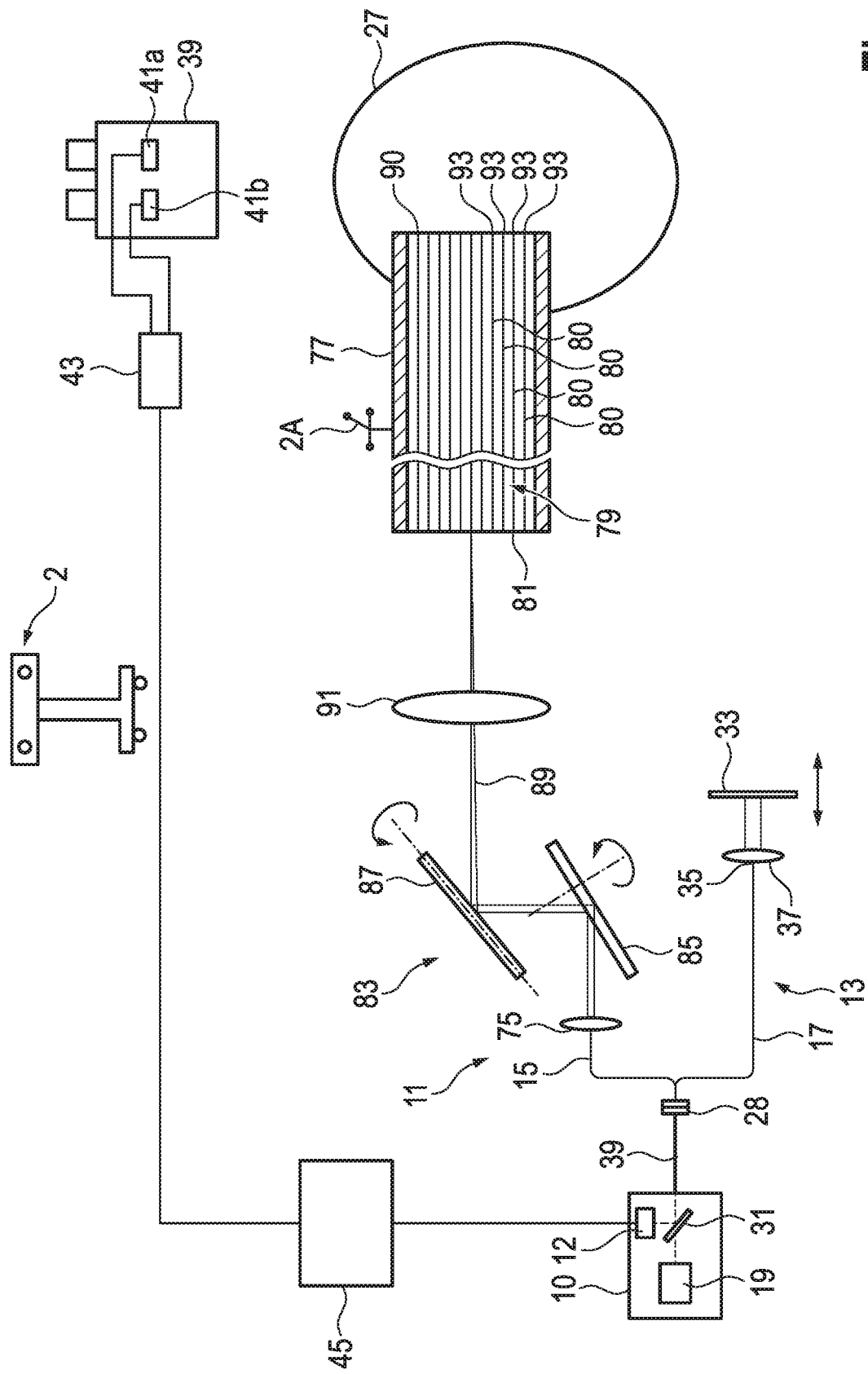
FIG. 12 shows a second exemplary embodiment of the microinstrument system, in which a fiber bundle is used instead of an individual optical fiber.
Figure 13:
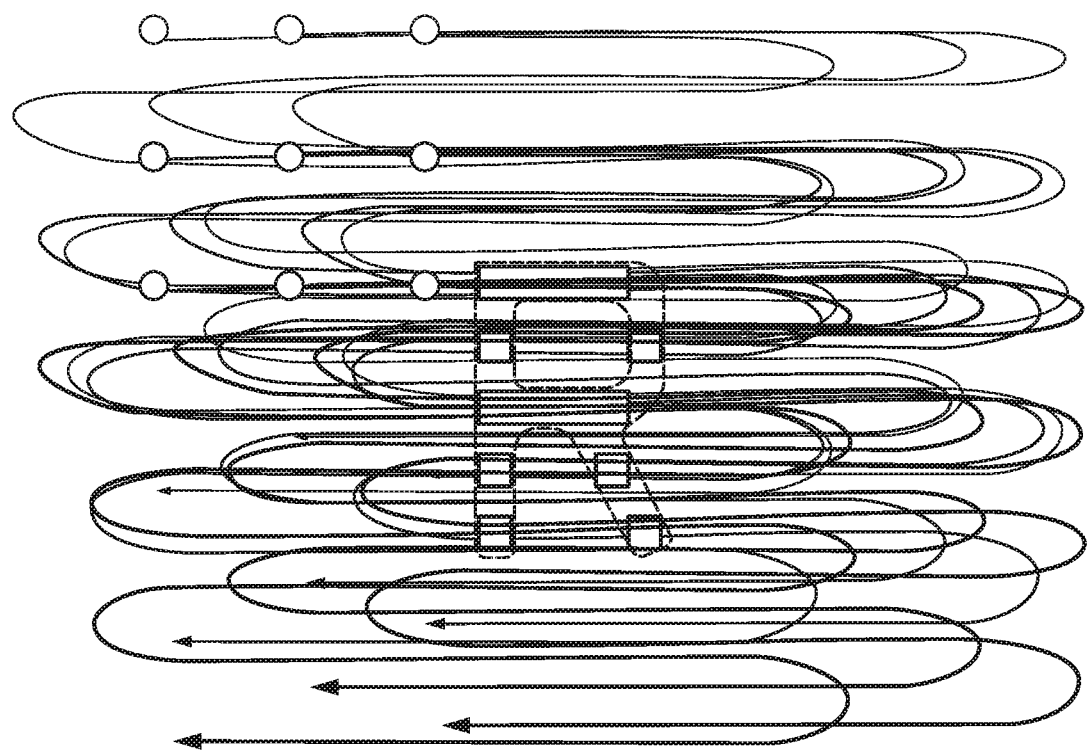
FIG. 13 shows a schematic illustration of the path of the distal end of the fiber bundle when recording a two-dimensional or three-dimensional image.
Figure 14:
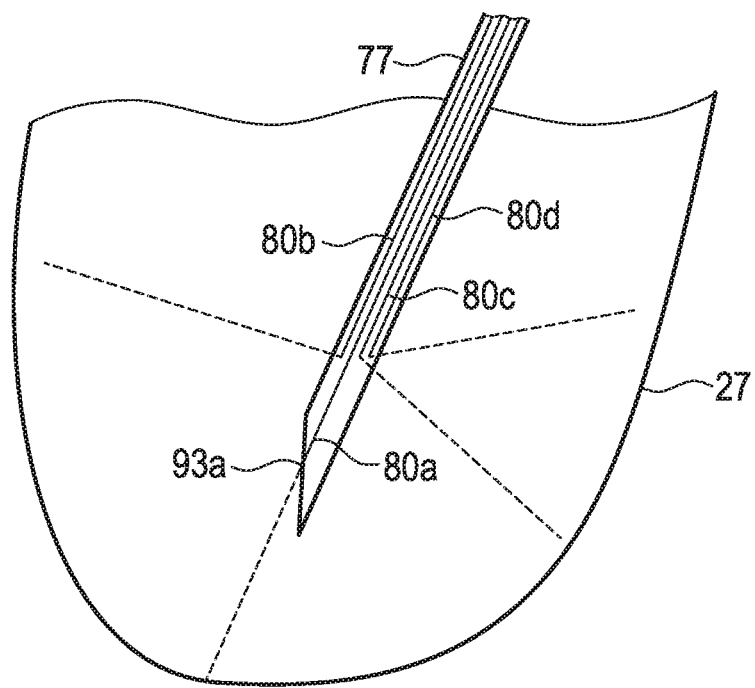
FIG. 14 shows an alternative configuration of the distal end of the microinstrument, as can be used in the second exemplary embodiment.
Figure 15:
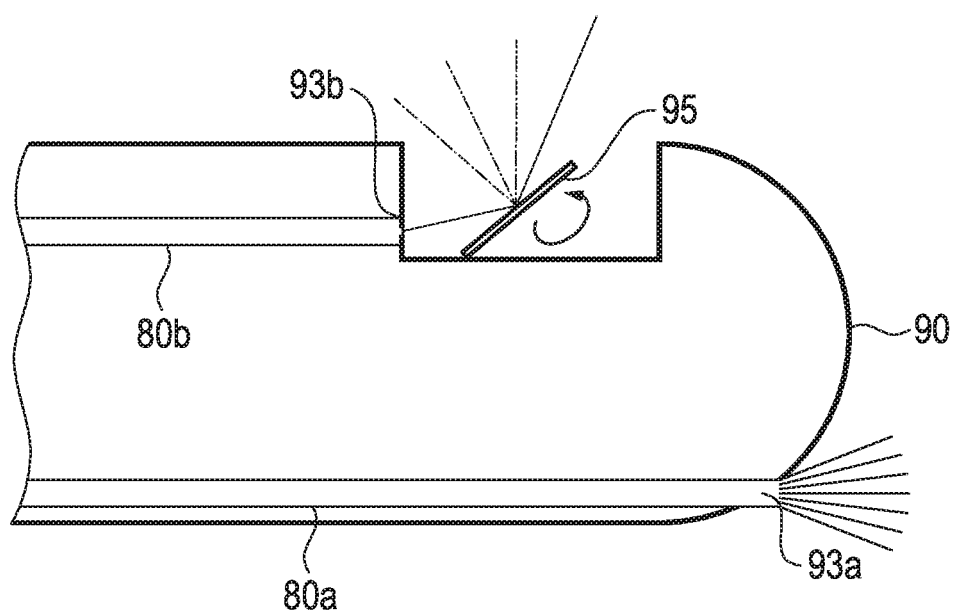
FIG. 15 shows an alternative option of recording two-dimensional or three-dimensional images when using a plurality of optical fibers.

A second exemplary embodiment of the microinstrument system according to the invention is described hereinafter with reference to FIGS. 12 to 15. In this case, FIG. 12 shows the microinstrument system and FIG. 13 shows the path of the distal end of the microinstrument system while recording a three-dimensional image. FIGS. 14 and 15 show modifications of the second exemplary embodiment.

The second exemplary embodiment of the microinstrument system according to the invention, depicted in FIG. 12, contains an OCT system with an object branch 11, a reference branch 13, and OCT hardware 10, like the first exemplary embodiment. The reference branch 13 and the OCT hardware 10 and the common fiber portion 29 do not differ from the reference branch 13, the OCT hardware 10 and the common fiber portion 29 of the first exemplary embodiment. They are therefore denoted by the same reference signs as in the first exemplary embodiment and are not described again, in order to avoid repetition. The surgical microscope 39, the evaluation unit 43, and the computer 45 likewise do not differ from those of the first exemplary embodiment. Therefore, these are likewise denoted by the reference signs from the first exemplary embodiment and are not described again either, in order to avoid repetition.

The second exemplary embodiment of the microinstrument system according to the invention differs from the first exemplary embodiment in terms of the design of the object branch 11 of the OCT system. Rather than guiding the optical fiber 15 up into the distal end of the microinstrument, the optical fiber 15 terminates in a collimation optical unit 75, which terminates upstream of the proximal end of a cannula 77 of a microinstrument. A fiber bundle 79 with a plurality of optical fibers 80 extends through the cannula 77. The fiber bundle 79 typically comprises at least two optical fibers 80, but no more than 1000 optical fibers 80. The number of optical fibers 80 of the fiber bundle 79 is restricted in this case by the space available in the cannula 77, which in turn is restricted by the external diameter of the cannula 77. In the present exemplary embodiment, the external diameter of the latter is 1.5 mm or less, preferably 1.0 mm or less, and in particular 0.6 mm or less. A handle, not shown in FIG. 12, which allows a treating surgeon to guide the microinstrument is located at the proximal end of the cannula 77.

A scanner 83, in the present exemplary embodiment comprising two drivable galvanometer mirrors 85, 87 that are rotatable about mutually perpendicular axes, is located between the collimation optical unit 75 of the optical fiber 15 of the object branch 11 and the proximal end 81 of the fiber bundle 79. In particular, this scanner 83 may also be arranged in the handle of the microinstrument. With the aid of the galvanometer mirrors 85, 87 of the scanner 83, it is possible to vary the position of the object light beam 89, which is collimated by the collimation optical unit 75, in the lateral direction upon incidence on a focusing optical unit 91. Depending on the position at which the collimated object light beam 89 is incident on the focusing optical unit 91, said object light beam is input coupled into a different optical fiber 80 of the fiber bundle 79. The light scattered back from the observation object 27 is then guided back to the focusing optical unit 91, which acts as a collimation optical unit in this direction, by this optical fiber. By way of the galvanometer mirrors 85, 87, the collimated object light beam is then directed at the collimation optical unit 75, which becomes a focusing optical unit in this direction and with the aid of which the collimated object light beam is focused at the end of the optical fiber 15.

Suitably driving the two galvanometer mirrors 85, 87 allows a lateral region of the observation object 27 to be scanned. The processing of the image data acquired by means of the individual optical fibers 80 of the fiber bundle 79 corresponds to the processing described with reference to the first exemplary embodiment. Since the positions and orientations of the distal ends 23 of the optical fibers 80 of the fiber bundle 79 are known relative to one another, a two-dimensional or three-dimensional image can be constructed from the A-scans recorded using the individual optical fibers 80 of the fiber bundle 79, the lateral extent of said image corresponding to the lateral extent of the arrangement of the distal ends 93 of the optical fibers in the fiber bundle 79. In contrast to the first exemplary embodiment, it is thus not merely A-scans that are recorded in the second exemplary embodiment when the distal end of the microinstrument is moved over the observation object 27, but B-scans if the distal ends 93 of the optical fibers 80 in the fiber bundle 79 are arranged along a line or a three-dimensional image if the distal ends 93 of the optical fibers 80 of the fiber bundle 79 are arranged in a planar manner.

Like in the first exemplary embodiment, the position and, if required, the orientation of the distal end 90 of the microinstrument during the movement over the region of interest of the observation objective 27 are also detected in the second exemplary embodiment with the aid of a tracking system 2 and the marker 2A of an inertial sensor system or with the aid of the image sensors 41A, 41B of the surgical microscope 39, as has already been explained with reference to the first exemplary embodiment. With the aid of the position data and optionally the orientation data, the image data recorded using the fiber bundle 79 when moving the distal end 90 of the microinstrument over the region of interest of the observation object 27 can be compiled to form a large two-dimensional or three-dimensional image, which is to say an image whose lateral extent is greater than the lateral extent of the arrangement of the distal ends of the optical fibers 80 in the fiber bundle 79.

However, determining the position data of the distal end 90 of the microinstrument by means of a navigation system 2, an inertial sensor system, or stereoscopic images is not necessary in the second exemplary embodiment. The recorded two-dimensional or three-dimensional images can be compiled to form a larger two-dimensional or three-dimensional image even without such a determination of the position data. What is exploited here is that the positions of the distal ends 93 of the individual optical fibers 80 in the fiber bundle 79 are known relative to one another. A planar arrangement of the distal ends 93 of the optical fibers in the fiber bundle 79 in particular leads to the individual optical fibers 80 successively sweeping over the same image regions when moving the distal end 90 of the microinstrument over the region of interest of the observation object 27. The paths of the individual optical fibers 80 of the fiber bundle 79 during this movement are depicted schematically in FIG. 13. If the frequency of the image recording now is so high that the object regions, which are imaged in the respective two-dimensional or three-dimensional images recorded during the movement of the distal end over the observation object 27, overlap one another, then the currently recorded two-dimensional or three-dimensional image in each case also images a part of the object region imaged in the preceding two-dimensional or three-dimensional image. By identifying structures in the object region imaged both in the current image and in the preceding image and by identifying the positions thereof in the respective images, it is possible to determine the positions and, if necessary, the orientations of the depicted object regions relative to the distal end of the fiber bundle. Position data and optionally orientation data can be determined for each image on the basis of the determined positions and optionally the determined orientations of the depicted object regions relative to the distal end of the fiber bundle and can then be used to compile the recorded two-dimensional or three-dimensional images to form a larger two-dimensional or three-dimensional image.

Although a two-dimensional or three-dimensional image can be compiled in the described manner, an image compiled in this manner cannot readily be superimposed on an image obtained preoperatively or postoperatively if the absolute position of the image is not known in a specific coordinate system. Therefore, it is advantageous if position data are also collected in this configuration, the position data determining the respective positions of the distal end 90 of the microinstrument in relation to a given coordinate system, which may be the coordinate system of the surgical microscope 39 in the present exemplary embodiment. Then, the recorded image can be superimposed on image data obtained preoperatively or postoperatively by means of suitable coordinate transformations. By contrast, the position detection in an entered coordinate system is not mandatory for simply overlaying the image data obtained with the OCT system on the stereoscopic image obtained using the surgical microscope 39 if the object regions identified in the images recorded with the OCT system can also be identified in the stereoscopic image of the surgical microscope. Then, the identified structures can be aligned for the purpose of overlaying the image obtained with the OCT system on the image obtained with the surgical microscope, whereby a positionally correct superimposition is made possible.

FIG. 14 shows a modification of the second exemplary embodiment. In this modification, the fiber bundle 79 only comprises four optical fibers 80*a*-*d*. Moreover, of these four optical fibers 80*a*-*d*, only one optical fiber 80*a* is guided up to the distal end 90 of the microinstrument or the cannula 77. This optical fiber 80*a* records image data along its longitudinal direction and serves for the actual recording of the image data which are compiled to form the two-dimensional or three-dimensional image. The remaining three optical fibers 80*b*-*c* already terminate before the distal end 90 of the microinstrument and collect the image data in their radial direction. In the embodiment variant shown in FIG. 14, these only serve to detect the position but not to collect the image data from which the two-dimensional or three-dimensional image is intended to be acquired.

With the aid of the image data acquired in the radial direction and in the longitudinal directions, it is then possible to determine the position and the orientation of the distal end 90 of the cannula within the observation object 27, which is to say within the eye in the present example. What can be exploited here is that the microinstrument or the cannula is generally inserted into the eye through a trocar which only allows a rotational movement about the trocar point, which is to say the point on the eyeball where the trocar is inserted into the eye, with the result that the distal end of the microinstrument or the cannula is moved on a spherical surface to a good approximation, for as long as it is not shifted along its longitudinal axis. Since the shape of the eyeball can be substantially determined on the basis of preoperative data, it is possible to determine the position of the distal end 90 of the microinstrument or the cannula around the eye from the determined distances of the distal ends of the four optical fibers 80*a*-*d* from the retina. With the aid of the positions and optionally orientations determined thus, it is then possible to compile the image data, collected in the longitudinal direction with the aid of the optical fiber 80*a*, to form a two-dimensional or three-dimensional image.

A modification of the variant of the second exemplary embodiment shown in FIG. 14 is shown in FIG. 15. Instead of four optical fibers 80*a*-*d*, the fiber bundle in the embodiment variant shown in FIG. 15 only comprises two optical fibers 80*a*, 80*b*. The distal end 93*b* of the optical fiber 80*b* is assigned a rotatable mirror 95 or any other scanning device, by means of which it is possible to vary the direction from which image data are collected with the aid of the optical fiber 80*b*. In this way, it is possible to acquire image data from different directions, which image data, like in the embodiment variant shown in FIG. 14, can be used to determine the position of the distal end 90 of the microinstrument, which is a vitrectome in the depicted variant, and hence determine the position of the distal end 93*a* of the optical fiber 80*a* in the observation object using the preoperatively determined geometry of the observation object.

The present invention has been described in detail on the basis of exemplary embodiments for purposes of explanation. However, a person skilled in the art recognizes that there can be deviations from the described embodiments within the scope of the present invention. In particular, the recording of an image need not be implemented with the aid of an OCT system but can also be realized with any other fiber-optic scanning system, for example a fiber-optic confocal laser scanning microscope. Moreover, the position data need not necessarily be determined using the surgical microscope. There is also the option of providing the microinstrument with a marker, the positioning of which relative to the distal end of the at least one optical fiber is known. By following the position of (tracking) the marker using a tracking system, it is possible at all times to determine the position data of the marker and hence the position of the distal end, which is known in relation to the position data of the marker. Moreover, relative position data may also be collected using acceleration sensors which detect the course of the movement of the distal end of the microinstrument. Possible further methods that can be used within the scope of the invention for collecting the position data include the projection of a pattern, for example in the infrared, onto the observation object, said pattern being identified in the recorded image data. The projected pattern can then find use as a reference for compiling the two-dimensional or three-dimensional image. Should the microinstrument be inserted into the observation object through a trocar, there is moreover the option of determining the position of the microinstrument in relation to a reference point on the trocar. If the position of the trocar is detected, for example by means of an external navigation system, then this also enables an absolute determination of the position of the distal end of the microinstrument. In the case of a vibration of the distal end of the microinstrument, it is possible to detect the curvature thereof with the aid of fiber Bragg gratings. The position of the distal end of the microinstrument relative to the proximal end can be determined from the curvature and the position of the fiber Bragg grating on the microinstrument. The two-dimensional or three-dimensional images acquired with the microinstrument system can moreover also be displayed as independent image data rather than being superimposed on other images like in the exemplary embodiments. Moreover, a plurality of position detection systems can be used simultaneously in order to increase the robustness of the position detection. Therefore, the present invention is not intended to be limited by the exemplary embodiments but rather only by the attached claims.

LIST OF REFERENCE SIGNS

1 Microinstrument
2 Navigation system
2A Marker
3 Cannula
5 Proximal end
7 Handle
9 Recording apparatus
10 Hardware
11 Object branch
12 Detector
13 Reference branch
15 Optical fiber
17 Optical fiber
19 Laser
21 Distal end
23 Distal end
25 Spot
27 Observation object
28 Coupler
29 Common fiber portion
31 Beam splitter
33 Mirror
35 Distal end
37 Collimation optical unit
39 Surgical microscope
41 A,B Image sensor
43 Evaluation unit
45 Computer
47 Piezo element
49 Piezo element
51 Optical fiber
52 Distal end 53 Vibrating galvanometer mirror
55 Object light beam
57 Proximal end
59 Shaft
61 Opening
63 Hollow tube
64 Reflective element
65 Distal end
66 Loop
67 Deflector
69 Transparent region
70 Inner surface
71 Guide rail
73 External wall
75 Collimation optical unit
77 Microinstrument
79 Fiber bundle
80 Optical fiber
81 Proximal end
83 Scanner
85 Galvanometer mirror
87 Galvanometer mirror
89 Collimated object light beam
90 Distal end
91 Focusing optical unit
93 Distal end
95 Rotatable mirror

The invention claimed is:

1. A microinstrument system for recording a two-dimensional or three-dimensional image of an observation object by fiber-optic scanning while the distal end of at least one optical fiber is moved laterally over the region of interest of the observation object with the aid of a microinstrument, comprising:
a microinstrument having at least one integrated optical fiber, which has a distal end to face the observation object,
a recording apparatus to which, for the purpose of recording image data, light from the observation object is suppliable with the aid of the at least one optical fiber,
a determination device designed to determine at least position data which represent the positions of the distal end of the at least one optical fiber at the recording times of the respective image data and to assign said position data to the image data; and
a data processing device, which
is connected to the recording apparatus for the purpose of receiving the image data;
is connected to the determination device for the purpose of receiving the position data; and
is designed to compile the image data to form a two-dimensional or three-dimensional image with the aid of the position data,
wherein the determination device is designed to determine the position data relative to the observation object.

2. The microinstrument system as claimed in claim 1, wherein:
the determination device is designed to also determine orientation data which represent the orientation of the distal end of the at least one optical fiber at the recording times of the respective image data and to assign said orientation data to the image data,
the data processing device is also connected to the determination device for the purpose of receiving the orientation data, and
the data processing device is designed to compile the image data to form a two-dimensional or three-dimensional image not only with the aid of the position data but also with the aid of the orientation data.

3. The microinstrument system as claimed in claim 1, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the determination device is a tracking system which is designed to determine the position data respectively from the detected position of an element of the microinstrument, of which the spatial position in relation to the distal end of the rod-shaped or tubular structure is known.

4. The microinstrument system as claimed in claim 1, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the determination device comprises an evaluation unit which is designed to identify, with the aid of image processing software, the distal end of the rod-shaped or tubular structure in stereoscopic images recorded by a surgical microscope and to determine the position data of the distal end of the rod-shaped or tubular structure in relation to the observation object or in relation to the coordinate system of the surgical microscope.

5. The microinstrument system as claimed in claim 1, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
an inertial sensor system finds use as a determination device, said inertial sensor system determining the position data on the basis of detected movements or on the basis of detected orientations.

6. The microinstrument system as claimed in claim 1, wherein a synchronization device designed, for the assignment of the position data and optionally the orientation data to the image data, to synchronize, firstly, the position data and optionally the orientation data and, secondly, the image data with one another in time.

7. The microinstrument system as claimed in claim 1, wherein a plurality of optical fibers, each with a distal end to face an observation object, are integrated into the microinstrument.

8. The microinstrument system as claimed in claim 1, wherein the microinstrument comprises a device for inducing a transverse vibration of the distal end of the at least one optical fiber or of the distal end of the microinstrument.

9. The microinstrument system as claimed in claim 8, wherein:
the device for introducing a vibration is designed such that it enables the induction of a transverse vibration with an adjustable orientation, and
the data processing device is designed to determine the vibration-corrected movement direction of the distal end of the at least one optical fiber or of the distal end of the microinstrument from temporally successive position data and optionally orientation data and to generate a control signal and output the latter to the device for inducing a vibration, said control signal controlling the device for inducing a vibration in such a way that the transverse vibration is oriented perpendicular to the determined vibration-corrected movement direction.

10. The microinstrument system as claimed in claim 1, wherein:
the microinstrument comprises a proximal end, at which the proximal end of the at least one optical fiber is located, and
in that a scanner is present at the proximal end or at the distal end of the microinstrument and can be used to modify the direction of the light emerging from the corresponding end of the at least one optical fiber and of the light entering the optical fiber.

11. The microinstrument system as claimed in claim 1, wherein:
a plurality of optical fibers are integrated in the microinstrument, and
the microinstrument comprises a scanner which is located at the proximal ends of the optical fibers and which can be used to sequentially input couple light into the proximal ends of the individual optical fibers and output couple light from the individual optical fibers.

12. A microinstrument system for recording a two-dimensional or three-dimensional image of an observation object by fiber-optic scanning while the distal end of at least one optical fiber is moved laterally over the region of interest of the observation object with the aid of a microinstrument, comprising:
a microinstrument having at least one integrated optical fiber, which has a distal end to face the observation object;
a recording apparatus to which, for the purpose of recording image data, light from the observation object is suppliable with the aid of the at least one optical fiber;
a determination device designed to determine at least position data which represent the positions of the distal end of the at least one optical fiber at the recording times of the respective image data and to assign said position data to the image data; and
a data processing device, which
is connected to the recording apparatus for the purpose of receiving the image data;
is connected to the determination device for the purpose of receiving the position data, and
is designed to compile the image data to form a two-dimensional or three-dimensional image with the aid of the position data, and
the determination device is designed to determine the position data absolutely in a defined coordinate system,
wherein:
the determination device is designed to also determine orientation data which represent the orientation of the distal end of the at least one optical fiber at the recording times of the respective image data and to assign said orientation data to the image data,
the data processing device is also connected to the determination device for the purpose of receiving the orientation data, and
the data processing device is designed to compile the image data to form a two-dimensional or three-dimensional image not only with the aid of the position data but also with the aid of the orientation data.

13. A computer-implemented method for generating a two-dimensional or three-dimensional image of an observation object with the aid of a microinstrument which is part of a fiber-optic scanning system and in which an optical fiber with a distal end to face the observation object is integrated, the method comprising the following steps:
receiving or retrieving a plurality of image data acquired with the aid of the at least one optical fiber, said image data being acquired while the distal end of the at least one optical fiber is moved laterally over the region of interest of the observation object with the aid of the microinstrument; and
receiving or retrieving at least position data assigned to the image data, said position data representing the positions of the distal end of the at least one optical fiber while the respective image data are acquired, or determining the position data from received or retrieved data, said data being assigned to the image data and allowing the position data of the distal end of the at least one optical fiber to be derived while the respective image data are acquired,
compiling the two-dimensional or three-dimensional image from the image data with the aid of the position data,
wherein the received, retrieved, or determined position data are available relative to the observation object.

14. The computer-implemented method as claimed in claim 13, wherein:
orientation data assigned to the image data, said orientation data representing the orientation of the distal end of the at least one optical fiber while the respective image data are acquired, are also received or recalled, or the orientation data are determined from received or retrieved data, said data being assigned to the image data and allowing the orientation data of the distal end of the at least one optical fiber to be derived while the respective image data are acquired, and
the image data are compiled to form the two-dimensional or three-dimensional image not only with the aid of the position data but also with the aid of the orientation data.

15. The computer-implemented method as claimed in claim 13, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the position data are received by a determination device which is a tracking system which is designed to determine the position data respectively from the detected position of an element of the microinstrument, of which the spatial position in relation to the distal end of the rod-shaped or tubular structure is known.

16. The computer-implemented method as claimed in claim 13, wherein:
  the microinstrument is a rod-shaped or tubular structure with a distal end, with the distal end of the optical fiber being located at the distal end of the rod-shaped or tubular structure,
  the lateral movement of the distal end of the at least one optical fiber over the region of interest of the observation object is implemented by virtue of the distal end of the rod-shaped or tubular structure being moved over the region of interest, and
  the position data are received by a determination device which comprises an evaluation unit which is designed to identify, with the aid of image processing software, the distal end of the rod-shaped or tubular structure in stereoscopic images recorded by a surgical microscope and to determine the position data of the distal end of the rod-shaped or tubular structure in relation to the observation object or in relation to the coordinate system of the surgical microscope.

17. The computer-implemented method as claimed in claim 13, wherein:
  the microinstrument is a rod-shaped or tubular structure with a distal end, with the distal end of the optical fiber being located at the distal end of the rod-shaped or tubular structure,
  the lateral movement of the distal end of the at least one optical fiber over the region of interest of the observation object is implemented by virtue of the distal end of the rod-shaped or tubular structure being moved over the region of interest, and
  the position data are received by a determination device designed an inertial sensor system, said inertial sensor system determining the position data on the basis of detected movements or on the basis of detected orientations.

18. The computer-implemented method as claimed in claim 13, wherein for the assignment of the position data and optionally the orientation data to the image data, firstly, the position data and optionally the orientation data and, secondly, the image data are synchronized with one another in time.

19. The computer-implemented method as claimed in claim 13, wherein moreover scanning data and/or vibration data are collected or retrieved, and the scanning data and/or vibration data are also taken into account when compiling the two-dimensional or three-dimensional image.

20. The computer-implemented method as claimed in claim 13, wherein the position data and optionally the orientation data are acquired from common image content of recorded image data.

21. A computer-implemented method for generating a two-dimensional or three-dimensional image of an observation object with the aid of a microinstrument which is part of a fiber-optic scanning system and in which an optical fiber with a distal end to face the observation object is integrated, the method comprising the following steps:
  receiving or retrieving a plurality of image data acquired with the aid of the at least one optical fiber, said image data being acquired while the distal end of the at least one optical fiber is moved laterally over the region of interest of the observation object with the aid of the microinstrument; and
  receiving or retrieving at least position data assigned to the image data, said position data representing the positions of the distal end of the at least one optical fiber while the respective image data are acquired, or determining the position data from received or retrieved data, said data being assigned to the image data and allowing the position data of the distal end of the at least one optical fiber to be derived while the respective image data are acquired,
  compiling the two-dimensional or three-dimensional image from the image data with the aid of the position data,
  wherein:
  the received, retrieved, or determined position data are available absolutely in a defined coordinate system,
  orientation data assigned to the image data, said orientation data representing the orientation of the distal end of the at least one optical fiber while the respective image data are acquired, are also received or retrieved, or the orientation data are determined from received or retrieved data, said data being assigned to the image data and allowing the orientation data of the distal end of the at least one optical fiber to be derived while the respective image data are acquired, and
  the image data are compiled to form the two-dimensional or three-dimensional image not only with the aid of the position data but also with the aid of the orientation data.

22. A method for recording a two-dimensional or three-dimensional image of a region of interest of an observation object by fiber-optic scanning using a microinstrument in which at least one optical fiber with a distal end to face the observation object is integrated and while the distal end of the at least one optical fiber is moved over the region of interest of the observation object with the aid of the microinstrument, the method comprising the following steps:
  collecting position data for a number of positions on the path along which the distal end of the at least one optical fiber is moved during the movement over the region of interest of the observation object, or collecting data from which it is possible to derive position data for a number of positions on the path along which the distal end of the at least one optical fiber is moved during the movement over the region of interest of the observation object and determining the position data from these data;
  collecting image data at positions for which the position data have been collected or determined, and assigning the image data to the respective position data; and
  compiling the image data to form the two-dimensional or three-dimensional image with the aid of the position data,
  wherein the collected or determined position data are available relative to the observation object.

23. The method as claimed in claim 22, wherein:
  orientation data for the number of positions on the path along which the distal end of the at least one optical fiber is moved during the movement over the region of interest of the observation object are collected, or the orientation data are determined from data from which it is possible to derive orientation data for the number of positions on the path along which the distal end of the at least one optical fiber is moved during the movement over the region of interest of the observation object;
  the image data are assigned not only to the respective position data but also to the respective orientation data; and the image data are compiled to form the two-dimensional or three-dimensional image not only with the aid of the position data but also with the aid of the orientation data.

24. The method as claimed in claim 23, wherein the direction of the light supplied to the distal end of the at least one optical fiber for the purpose of recording the image data is modified while the distal end of the at least one optical fiber is moved over the region of interest of the observation object with the aid of the microinstrument.

25. The method as claimed in claim 22, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the position data are collected by virtue of a determination device, which is a tracking system, determining the position data respectively from the detected position of an element of the microinstrument, of which the spatial position in relation to the distal end of the rod-shaped or tubular structure is known.

26. The method as claimed in claim 22, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the position data are collected by virtue of a determination device, which comprises an evaluation unit with image processing software, identifying, with the aid thereof, the distal end of the rod-shaped or tubular structure in stereoscopic images recorded by a surgical microscope and the position data being determined on the basis of stereoscopic information of the distal end of the rod-shaped or tubular structure in relation to the observation object or in relation to the coordinate system of the surgical microscope.

27. The method as claimed in claim 22, wherein:
the microinstrument is a rod-shaped or tubular structure with a distal end, with the distal end of the optical fiber being located at the distal end of the rod-shaped or tubular structure,
the lateral movement of the distal end of the at least one optical fiber over the region of interest of the observation object is implemented by virtue of the distal end of the rod-shaped or tubular structure being moved over the region of interest, and
the position data are collected by virtue of an inertial sensor system finding use as a determination device, said inertial sensor system determining the position data on the basis of detected movements or on the basis of detected orientations.

28. The method as claimed in claim 22, characterized in that for the assignment of the position data and optionally the orientation data to the image data, firstly, the position data and optionally the orientation data and, secondly, the image data are synchronized with one another in time.

29. The method as claimed in claim 22, wherein use is made of a microinstrument in which a plurality of optical fibers, each with a distal end to face the observation object, are integrated, and image data are acquired by each of the optical fibers at the positions for which position data were collected.

30. The method as claimed in claim 22, wherein a transverse vibration of the at least one distal end of the at least one optical fiber or of the distal end of the microinstrument is induced, and the position data are collected at different positions of the distal end of the at least one optical fiber during a vibration period of the induced vibration.

31. A method for recording a two-dimensional or three-dimensional image of a region of interest of an observation object by fiber-optic scanning using a microinstrument in which at least one optical fiber with a distal end to face the observation object is integrated and while the distal end of the at least one optical fiber is moved over the region of interest of the observation object with the aid of the microinstrument, the method comprising the following steps:
collecting position data for a number of positions on the path along which the distal end of the at least one optical fiber is moved during the movement over the region of interest of the observation object, or collecting data from which it is possible to derive position data for a number of positions on the path along which the distal end of the at least one optical fiber is moved during the movement over the region of interest of the observation object and determining the position data from these data;
collecting image data at positions for which position data have been collected or determined, and assigning the image data to the respective position data; and
compiling the image data to form the two-dimensional or three-dimensional image with the aid of the position data,
wherein:
the collected or determined position data are available absolutely in a defined coordinate system,
orientation data for the number of positions on the path along which the distal end of the at least one optical fiber is moved during the movement over the region of interest of the observation object are collected, or the orientation data are determined from data from which it is possible to derive orientation data for the number of positions on the path along which the distal end of the at least one optical fiber is moved during the movement over the region of interest of the observation object;
the image data are assigned not only to the respective position data but also to the respective orientation data; and
the image data are compiled to form the two-dimensional or three-dimensional image not only with the aid of the position data but also with the aid of the orientation data.

32. The method as claimed in claim 31, wherein the current, vibration-corrected direction of the path, along which the distal end of the at least one optical fiber or the distal end of the microinstrument is moved during the movement over the region of interest of the observation object, is determined from the position data and the transverse vibration of the distal end of the at least one optical fiber or of the distal end of the microinstrument a transverse vibration is induced, which runs perpendicular to the determined current, vibration-corrected direction.

\* \* \* \* \*